US011617568B2

United States Patent
Joshi et al.

(10) Patent No.: US 11,617,568 B2
(45) Date of Patent: Apr. 4, 2023

(54) FLUID OUTPUT MEASUREMENT DEVICE AND METHOD

(71) Applicants: Jay K. Joshi, Chicago, IL (US); Alex S. Holterman, Chicago, IL (US); Jordan D. Altman, Chicago, IL (US); Antonio J. Belton, Richton Park, IL (US); Sean J. Corrigan, Chicago, IL (US); Keith A. Grider, Chicago, IL (US); Daniel J. Greene, Chicago, IL (US); Stephen J. McPhilliamy, Chicago, IL (US); Marcus S. Papadopoulos, Chicago, IL (US); Michael C. Garrett, Wilmette, IL (US); Frank E. Garrett, Jr., Barrington, IL (US); Brian J. Skelton, Lake Zurich, IL (US); William E. Shaw, Palatine, IL (US); Tomas A. Matusaitis, Chicago, IL (US)

(72) Inventors: Jay K. Joshi, Chicago, IL (US); Alex S. Holterman, Chicago, IL (US); Jordan D. Altman, Chicago, IL (US); Antonio J. Belton, Richton Park, IL (US); Sean J. Corrigan, Chicago, IL (US); Keith A. Grider, Chicago, IL (US); Daniel J. Greene, Chicago, IL (US); Stephen J. McPhilliamy, Chicago, IL (US); Marcus S. Papadopoulos, Chicago, IL (US); Michael C. Garrett, Wilmette, IL (US); Frank E. Garrett, Jr., Barrington, IL (US); Brian J. Skelton, Lake Zurich, IL (US); William E. Shaw, Palatine, IL (US); Tomas A. Matusaitis, Chicago, IL (US)

( * ) Notice: Subject to any disclaimer, the term of this patent is extended or adjusted under 35 U.S.C. 154(b) by 151 days.

(21) Appl. No.: 15/852,578

(22) Filed: Dec. 22, 2017

(65) Prior Publication Data
US 2018/0338747 A1    Nov. 29, 2018

Related U.S. Application Data

(60) Provisional application No. 62/440,113, filed on Dec. 29, 2016.

(51) Int. Cl.
*A61B 10/00* (2006.01)
*A61B 5/20* (2006.01)

(52) U.S. Cl.
CPC ............ *A61B 10/007* (2013.01); *A61B 5/207* (2013.01); *A61B 5/208* (2013.01)

(58) Field of Classification Search
CPC .......... A61B 2562/0295; A61B 10/007; A61B 5/207; A61B 5/208; A61B 5/1411;
(Continued)

(56) References Cited

U.S. PATENT DOCUMENTS 3,345,980 A    10/1967 Coanda
3,906,958 A     9/1975 Knox
(Continued)

FOREIGN PATENT DOCUMENTS

WO    WO 2014/043650 A2    3/2014

*Primary Examiner* — Alex M Valvis
*Assistant Examiner* — Chanel J Jhin
(74) *Attorney, Agent, or Firm* — Frost Brown Todd LLC

(57) ABSTRACT

An apparatus includes a disposable assembly and a reusable assembly. The disposable assembly includes a fluid input port, a fluid output port, and a tube configured to provide fluid communication between the fluid input port and the fluid output port. The reusable assembly includes a housing, a fluid management assembly that is configured to transition between an open position and a closed position, and a sensing assembly. The fluid management assembly is configured to prevent fluid from traveling past the tube to the (Continued)

fluid output port in the closed position. The sensing assembly is configured to sense fluid accumulating within the tube while the fluid management assembly is in the closed position. The sensing assembly is also configured to drive the fluid management assembly from the closed position to the open position when the sensing assembly detects fluid within the tube at a predetermined range.

20 Claims, 36 Drawing Sheets

(58) Field of Classification Search
CPC ... A61B 5/1422; A61B 5/145; A61B 5/14503; A61B 5/14507; A61B 5/1451; A61B 5/14517; A61B 5/14532; A61B 5/14535; A61B 5/14539; A61B 5/14542; A61B 5/14546; A61B 5/1455; A61B 5/14551; A61B 5/1468; A61B 5/1486; A61B 5/157; A61B 10/0045
USPC .......................................................... 600/584
See application file for complete search history.

(56) References Cited

U.S. PATENT DOCUMENTS

| | | | |
|---|---|---|---|
| 4,051,431 A | 9/1977 | Wurster | |
| 4,099,412 A | 7/1978 | Nehrbass | |
| D252,470 S | 7/1979 | Pawlak | |
| 4,291,706 A | 9/1981 | Voges et al. | |
| 4,343,316 A * | 8/1982 | Jespersen | A61B 5/201 |
| | | | 600/575 |
| 4,532,936 A | 8/1985 | LeVeen et al. | |
| 4,891,993 A | 1/1990 | Barker | |
| 5,176,148 A | 1/1993 | Wiest et al. | |
| 5,602,038 A | 2/1997 | Kell | |
| 5,769,087 A | 6/1998 | Westphal et al. | |
| 5,772,606 A | 6/1998 | Ashibe et al. | |
| 6,151,522 A | 11/2000 | Alfano et al. | |
| 6,490,920 B1 | 12/2002 | Netzer | |
| 6,658,946 B2 | 12/2003 | Lipscomb et al. | |
| 6,851,453 B2 | 2/2005 | Lipscomb et al. | |
| 6,856,146 B2 | 2/2005 | Bo | |
| 6,925,398 B2 | 8/2005 | McDermid | |
| 7,002,670 B2 | 2/2006 | Wariar et al. | |
| 7,030,768 B2 | 4/2006 | Wanie | |
| 7,129,715 B2 | 10/2006 | Hayashi et al. | |
| 7,258,005 B2 | 8/2007 | Nyce | |
| 7,324,901 B2 | 1/2008 | McDermid | |
| 7,739,907 B2 | 6/2010 | Boiarski et al. | |
| 7,931,630 B2 | 4/2011 | Nishtala et al. | |
| 8,424,376 B2 | 4/2013 | Boiarski | |
| 8,471,231 B2 | 6/2013 | Paz | |
| 8,663,128 B2 | 3/2014 | Paz et al. | |
| 8,715,254 B2 | 5/2014 | Nishtala | |
| 8,813,551 B2 | 8/2014 | Boiarski | |
| 8,827,924 B2 | 9/2014 | Paz et al. | |
| 9,642,967 B2 * | 5/2017 | Ribble | A61B 5/1117 |
| 2002/0161314 A1 | 10/2002 | Sarajarvi | |
| 2005/0247121 A1 | 11/2005 | Pelster | |
| 2006/0100743 A1 | 5/2006 | Townsend et al. | |
| 2006/0212024 A1 | 9/2006 | Blake et al. | |
| 2007/0101811 A1 | 5/2007 | Nyce et al. | |
| 2008/0210229 A1 | 9/2008 | Corbacho | |
| 2008/0319374 A1 * | 12/2008 | Zacharias | A61M 1/743 |
| | | | 604/22 |
| 2010/0240964 A1 * | 9/2010 | Sterling | A61B 5/14532 |
| | | | 600/300 |
| 2011/0265889 A1 | 11/2011 | Tanaka et al. | |
| 2014/0116128 A1 | 5/2014 | Mantinband et al. | |
| 2014/0155782 A1 * | 6/2014 | Bullington | A61B 5/157 |
| | | | 600/575 |
| 2014/0163340 A1 * | 6/2014 | Say | A61B 5/6866 |
| | | | 600/309 |
| 2015/0362351 A1 * | 12/2015 | Joshi | A61B 10/007 |
| | | | 700/282 |
| 2016/0324454 A1 * | 11/2016 | Bullington | A61B 5/157 |

* cited by examiner

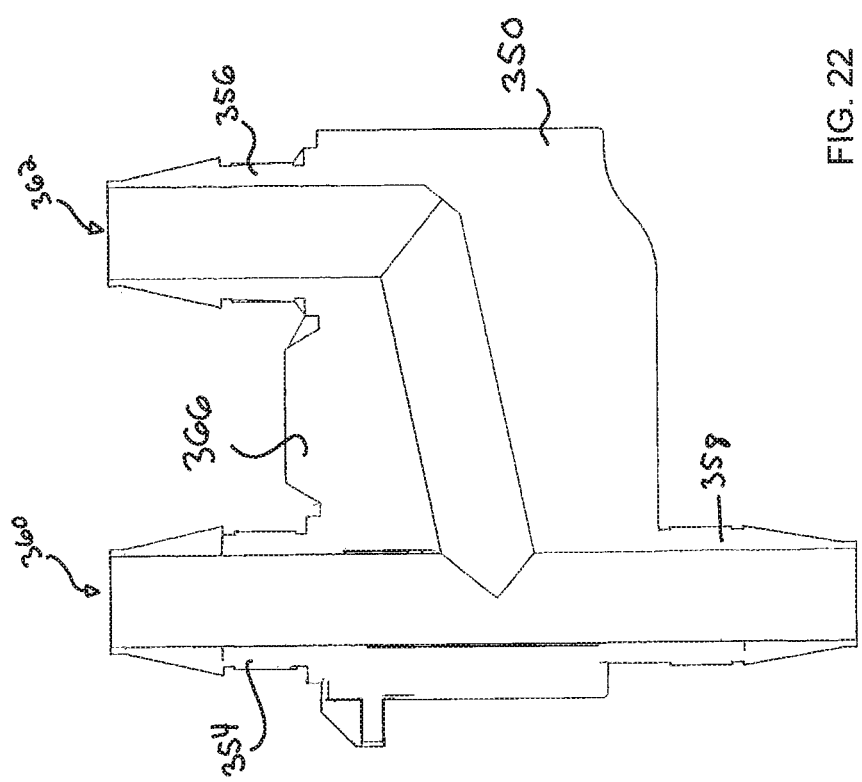

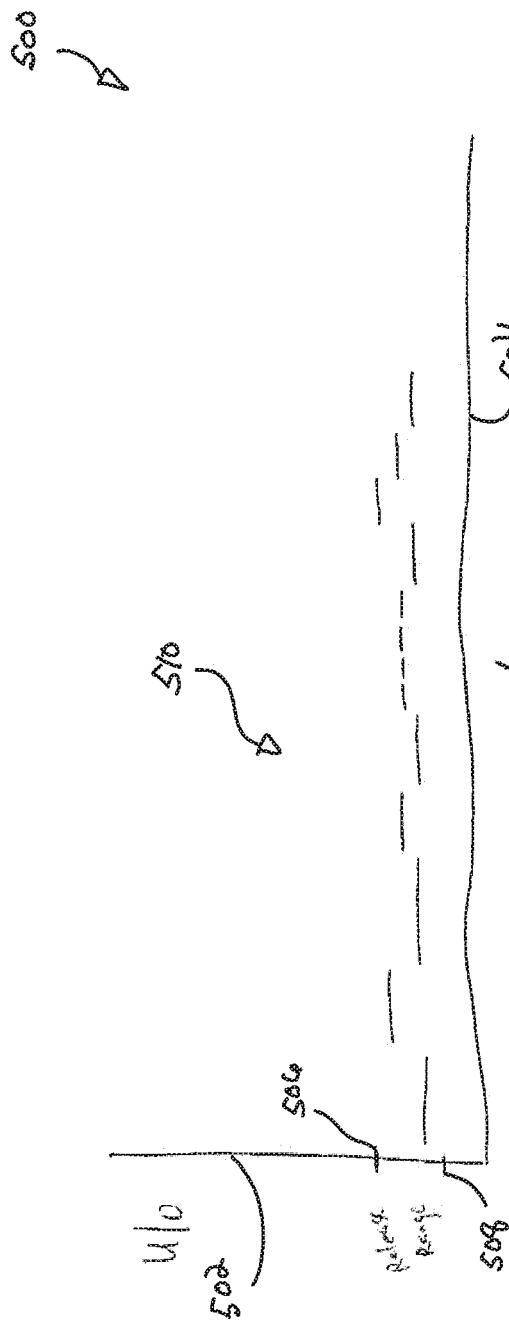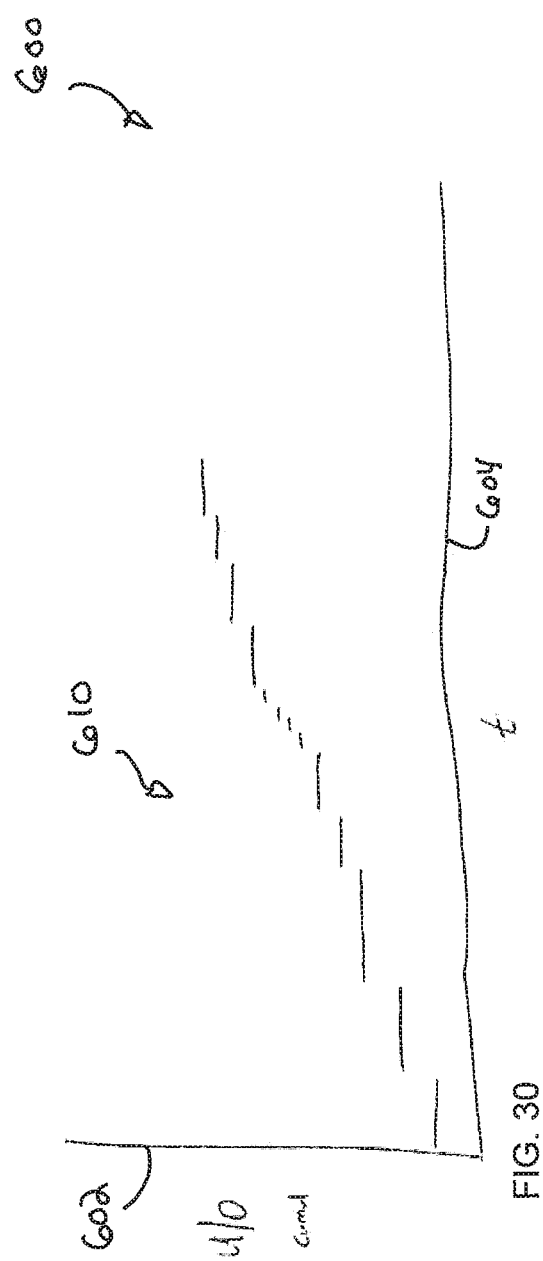

FLUID OUTPUT MEASUREMENT DEVICE AND METHOD

PRIORITY

This application claims priority to U.S. Provisional Pat. App. No. 62/440,113, entitled "Fluid Output Measurement Device and Method," filed Dec. 29, 2016, the disclosure of which is incorporated by reference herein.

BACKGROUND

In some settings, human body fluid output measurements and analysis may be essential to clinical management and translational research. Patient care may require diligent evaluation of output and analysis of human body fluid output in order to assess optimal fluid balances, loss of fluid, and sources and courses of fluid output and/or fluid loss.

Using conventional techniques, patient fluid outputs may be measured by medical staff with containers/bags having markings corresponding to a particular output. Medical staff may measure the fluid output by comparing the fluid level to the markings on the container/bag. With this comparison, medical staff may ascertain, to the best of their ability, the volume of fluid within the container/bag. Medical staff may also compare the volume of fluid within the container/bag to the time it took to reach that volume of fluid in order to predict an average volumetric flow rate. However, because humans perform these tasks through visual comparison and mental calculation or hand calculation, any number of human errors may arise, such as misreading fluid levels or miscalculating average flow rates.

In some cases, patient fluid may be collected over an extended period of time where the volumetric flow rate of the fluid varies over the collection period. As one merely illustrative example, medical staff may utilize a catheter and collection bag over an extended period to collect urine from a patient. Urine may transfer through the catheter and toward the collection bag at varying volumetric flow rates. For some periods, no urine may transfer through the catheter toward the collection bag; while for other periods, there may be low to high urine output.

Urine output is an important vital sign used in treating patients with an Acute Kidney Injury. There may be a correlation between the mortality rate associated with Acute Kidney Injury and the frequency/duration of low urine output episodes. Therefore, it may be useful to automatically and accurately measure urine output, volumetric flow rate of urine output; and change in volumetric flow rate of urine output in order to more acutely diagnose risk factors associated with those metrics.

Urine is just one example of human bodily fluid output that may be analyzed. Any other type of human bodily fluid output may be measured in fluid output, volumetric flow rate, and change in volumetric flow rate for any number of analyses.

While various kinds of fluid output measurement devices, methods, and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 22 depicts a cross-sectional front view of the fluid output fitting of FIG. 21, taken along line 22-22 of FIG. 21;

FIG. 29 depicts a graph representing individual fluid outputs from the fluid output measuring device of FIG. 2;

FIG. 30 depicts a graph representing a cumulative fluid output from the fluid output measuring device of FIG. 2 over a period of time.

Figure 1:
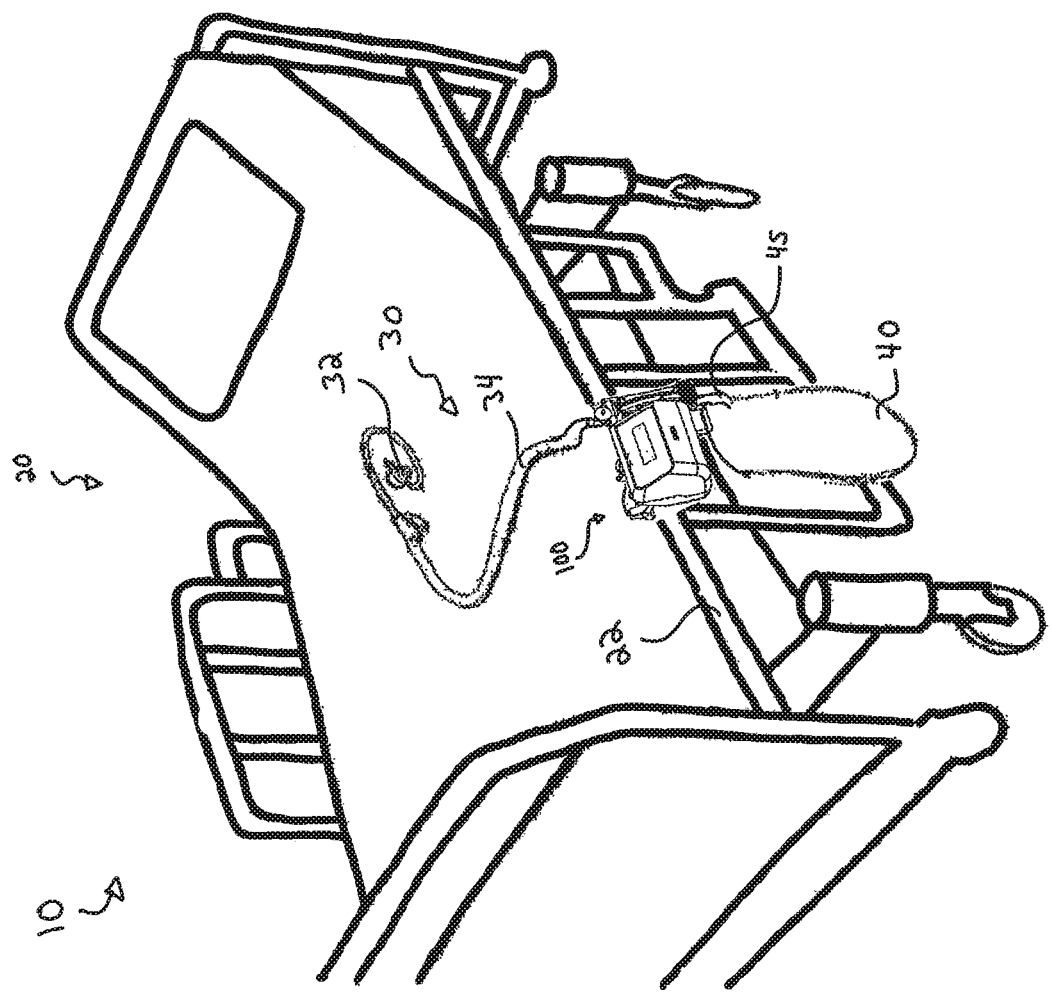
FIG. 1 depicts a perspective view of an exemplary patient station.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Exemplary Patient Station

FIG. 1 shows an exemplary patient station (10). Patient station (10) may receive and store bodily fluids from a patient while allowing the patient to rest. Patient station (10) includes a bed assembly (20), a catheter assembly (30), and a fluid output measuring device (100) in fluid communication with and between components of catheter assembly (30). Catheter assembly (30) is configured to extract and store urine from a patient. Catheter assembly (30) includes a catheter (32) in fluid communication with an input fluid tube (32), and a collection bag (40) in fluid communication with an output fluid tube (45). Catheter assembly (30) may include any other suitable components known to a person having ordinary skill in the art in view of the teachings herein. Input fluid tube (32) and output fluid tube (45) are both in fluid communication with fluid output measuring device (100) such that fluid output measuring device (100) provides fluid communication between input fluid tube (32) and output fluid tube (45). Therefore, fluid output measuring device (100) is configured to receive fluid that travels from catheter (32), through input fluid tube (34), process the received fluid, and then transfer the fluid to output fluid tube (45), which in turn transfers the fluid to collection bag (40).

As will be described in greater detail below, fluid output measuring device (100) includes a reusable assembly (200) and a disposable assembly (300). Disposable assembly (300) is the portion of fluid output measuring device (100) in fluid communication with catheter assembly (30). Additionally, disposable assembly (300) may be selectively attachable to reusable assembly (200) such that reusable assembly (200) may support disposable assembly (300). Any suitable type of catheter (32), input fluid tube (32), output fluid tube (45), and collection bag (40) may be used in conjunction with disposable assembly (300) as will be apparent to one having ordinary skill in the art in view of the teachings herein. For example, in some versions of fluid output measuring device (100), conventional catheters (e.g., Foley catheters, etc.) and conventional urine collection bags may be incorporated for use with disposable assembly (300). Alternatively, a modified version of a conventional catheter and/or a modified version of a conventional urine collection bag may be incorporated for use with disposable assembly (300). The invention is not intended to be necessarily limited to use with a particular kind of catheter or urine collection bag.

The entirety of catheter assembly (30), or selected portions thereof, may be modified, assembled, and sterilized with disposable assembly (300), such that disposable assembly (300) and catheter assembly (30) act as a single replaceable unit. Alternatively, catheter assembly (30) may be provided separately of disposable assembly (300) such that an operator may assemble catheter assembly (30) with reusable assembly (300) prior to or immediately after attaching disposable assembly (300) with reusable assembly (200). Similarly, collection bag (40) may be provided as a pre-connected integral unit of disposable assembly (300), such that collection bag (40) is sterilized and packaged with the rest of disposable assembly (300) as a single unit. As another merely illustrative example, collection bag (40) may be provided as a non-connected separate part of a kit with the rest of disposable assembly (300), such that collection bag (40) is connected with the rest of disposable assembly (300) at the point of use. Alternatively, collection bag (40) may be provided separately from the rest of disposable assembly (300) (i.e., not in a kit with the rest of disposable assembly (300)), then assembled with the rest of disposable assembly (300) at the point of use. In any case, it should be understood that catheter assembly (30), collection bag (40), and the rest of disposable assembly (300) may all be disposed of after use. Moreover, collection bag (40) may contain a drainage valve such that an operator may drain accumulated fluid from collection bag (40) during use.

As will also be described in greater detail below, collection bag (40) is also selectively attachable to reusable assembly (200) of fluid output measuring device (100) such that collection bag (40) hangs or otherwise associates with reusable assembly (1200). Therefore, a user may physically attach collection bag (40) to fluid output measuring device (100). It should be understood that, when collection bag (40) is coupled with disposable assembly (300), collection bag (40) is in fluid communication with disposable assembly (300). By contrast, when collection bag (40) is coupled with reusable assembly (200), collection bag (40) is merely supported by reusable assembly (200) without being in fluid communication with reusable assembly (200).

Reusable assembly (300) of fluid output measuring device (100) is attached to a rail (22) of bed assembly (20) such that fluid output measuring device (100) is supported by rail (22) of bed assembly (20). However, it should be understood that fluid output measuring device (100) may be mechanically attached to other objects, such as an IV pole. Alternatively, fluid output measuring device (100) may be built into its own separate cabinet unit such that it is a stand-alone device. Fluid output measuring device (100) may be attached to any other suitable structure that would be apparent to one having ordinary skill in the art in view of the teachings herein.

Fluid output measuring device (100) may establish wireless communication with server (50). Server (50) may receive, store, and display data developed and acquired by fluid output measuring device (100). While in the current example, a server (50) is used to receive, store, and display data developed and acquired by fluid output measuring device (100), any other suitable device may be utilized as would be apparent to one having ordinary skill in the art in view of the teachings herein. For example, a smart phone, a laptop, tablet, or desktop may be used in place of server (50).

As will be described in greater detail below, fluid output measuring device (100) is configured to temporarily store and measure discrete amounts of fluid from catheter (32), then selectively transfer those discrete amounts of fluid to collection bag (40) after the fluid within fluid output measuring device (100) reaches a volume within a predetermined range. As will also be described in greater detail below, fluid output measuring device (100) is configured to store the volume associated with individual discrete amounts of transferred fluid to collection bag (40) and how long it took to accumulate the discrete amounts of transferred fluid. Fluid output measuring device (100) may utilize this data in order to calculate total volume within collection bag (40), volumetric flow rate of fluid leaving the patient at given points in time, change in volumetric flow rate of fluid leaving the patient at given points in time, and any other suitable calculations that would be apparent to one having ordinary skill in the art in view of the teachings herein.

While in the current example, patient station (10) is set up so that fluid output measuring device (100) is configured to receive urine from a patient via a catheter assembly (30), it should be understood that fluid output measuring device (100) may be configured to receive any number of fluids that would be apparent to one having ordinary skill in the art in view of the teachings herein.

II. Exemplary Fluid Output Measuring Device

Figure 2:
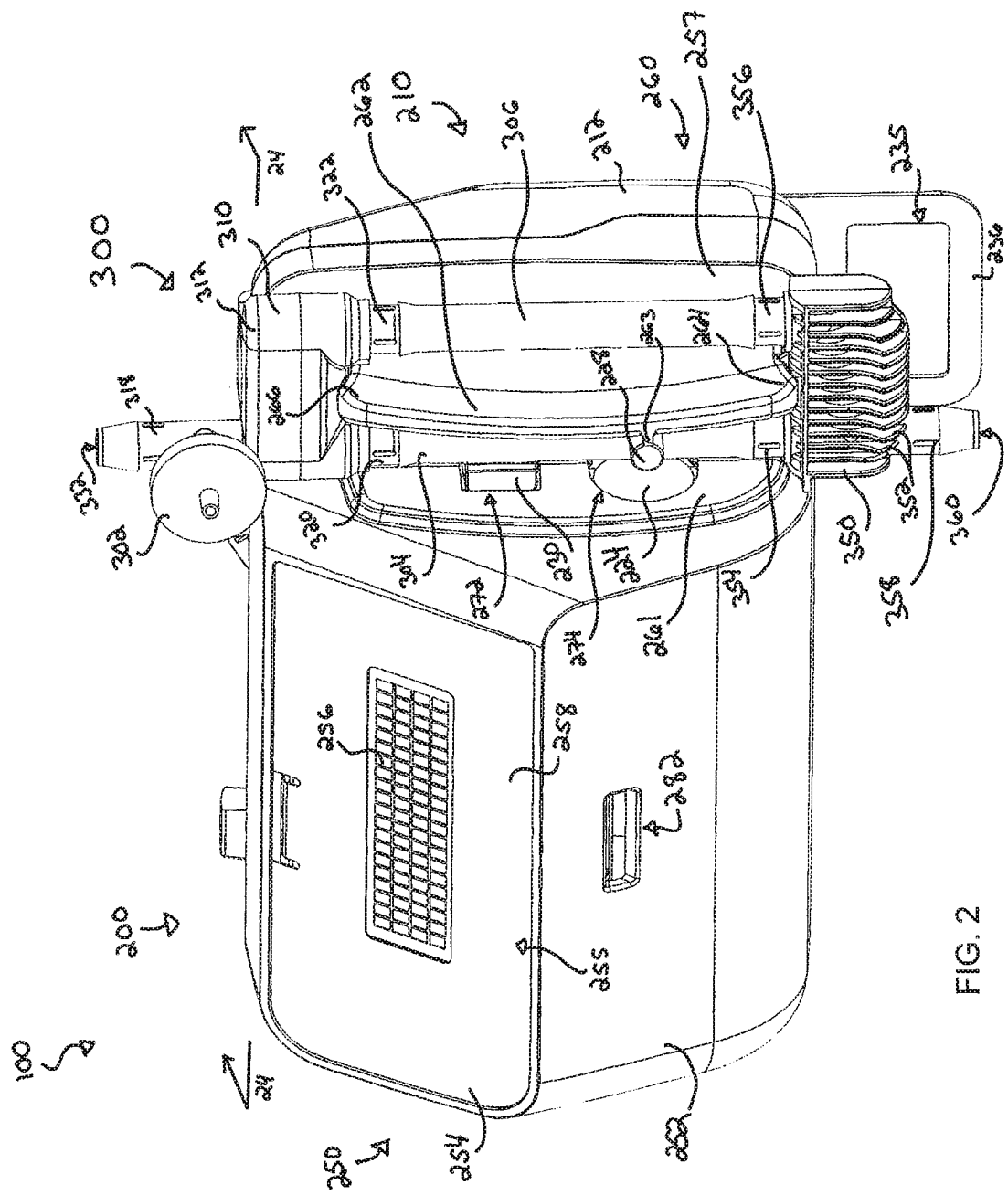
FIG. 2 depicts a perspective view of an exemplary fluid output measuring device of the patient station of FIG. 1.
Figure 3:
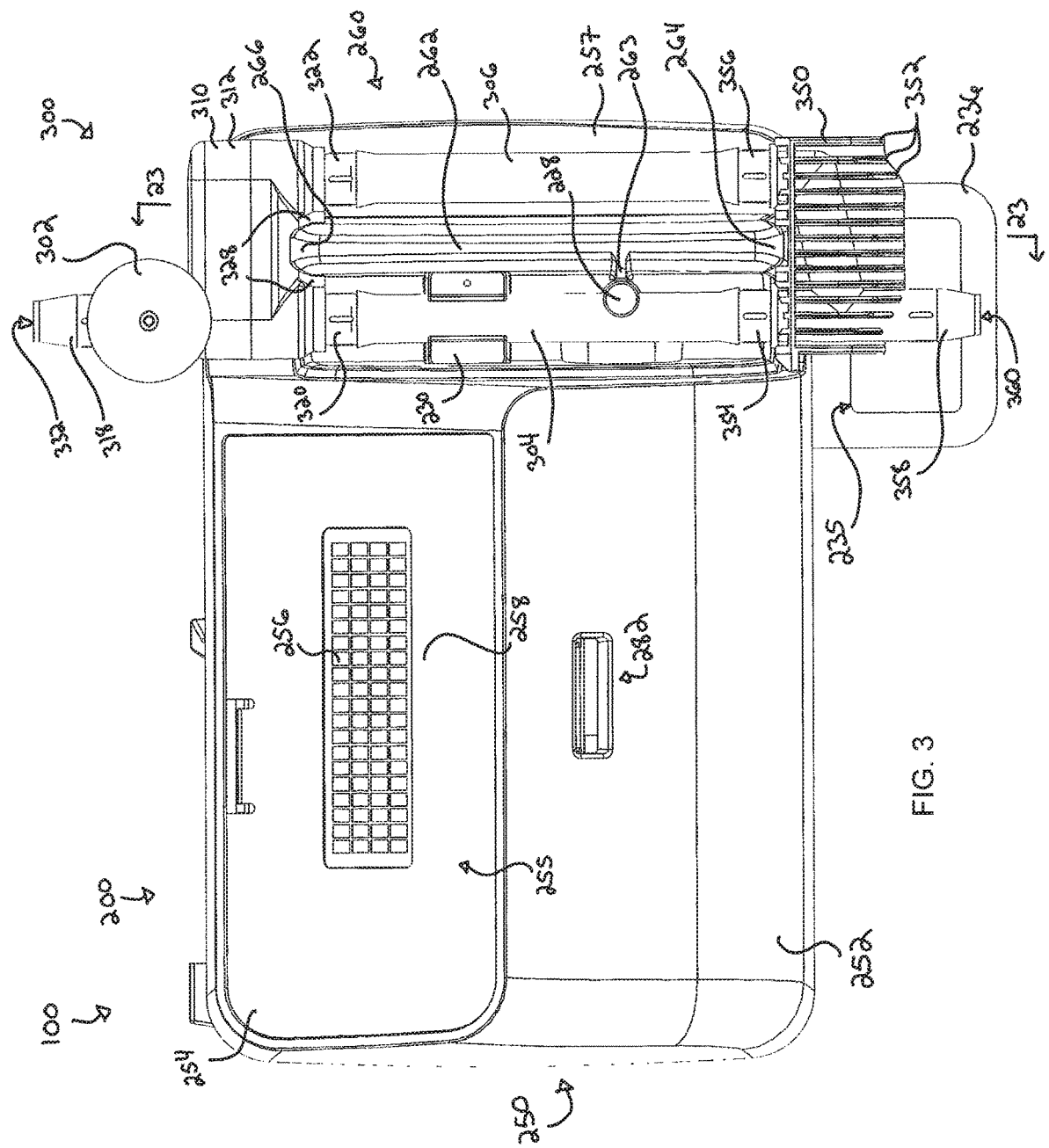
FIG. 3 depicts a front elevational view of the fluid output measuring device of FIG. 2.
Figure 4:
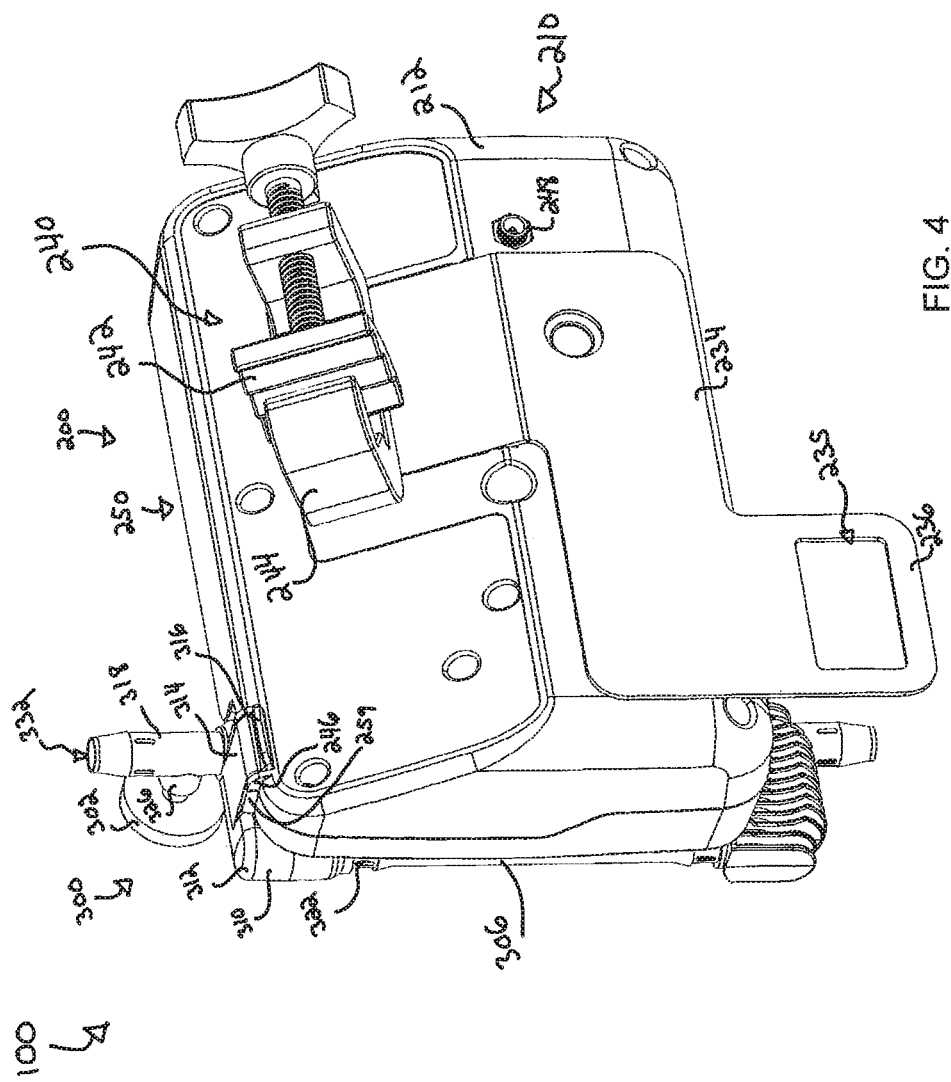
FIG. 4 depicts another perspective view of e fluid output measuring device of FIG. 2.
Figure 5:
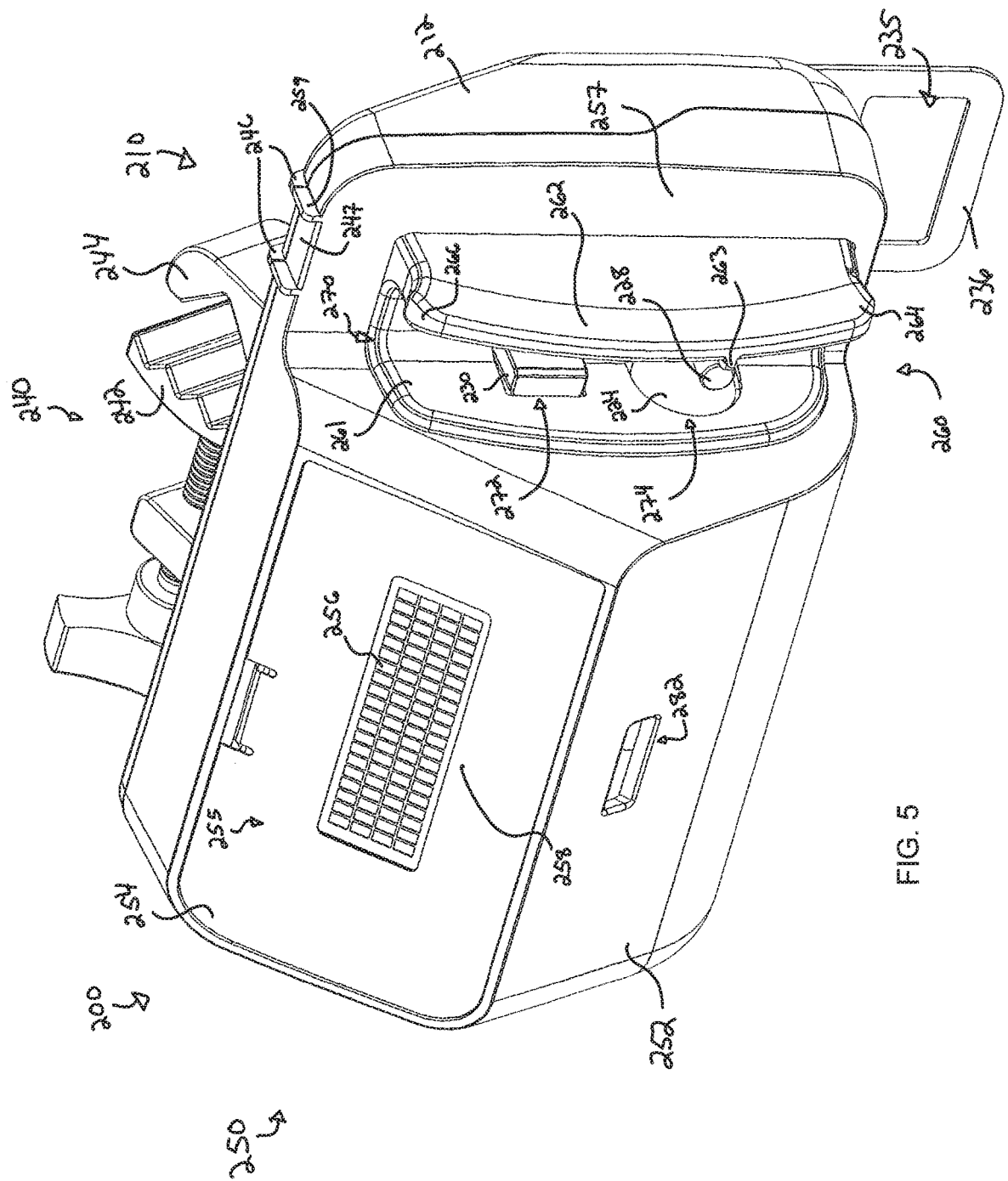
FIG. 5 depicts a perspective view of a reusable assembly of the fluid output measuring device of FIG. 2.
Figure 6:
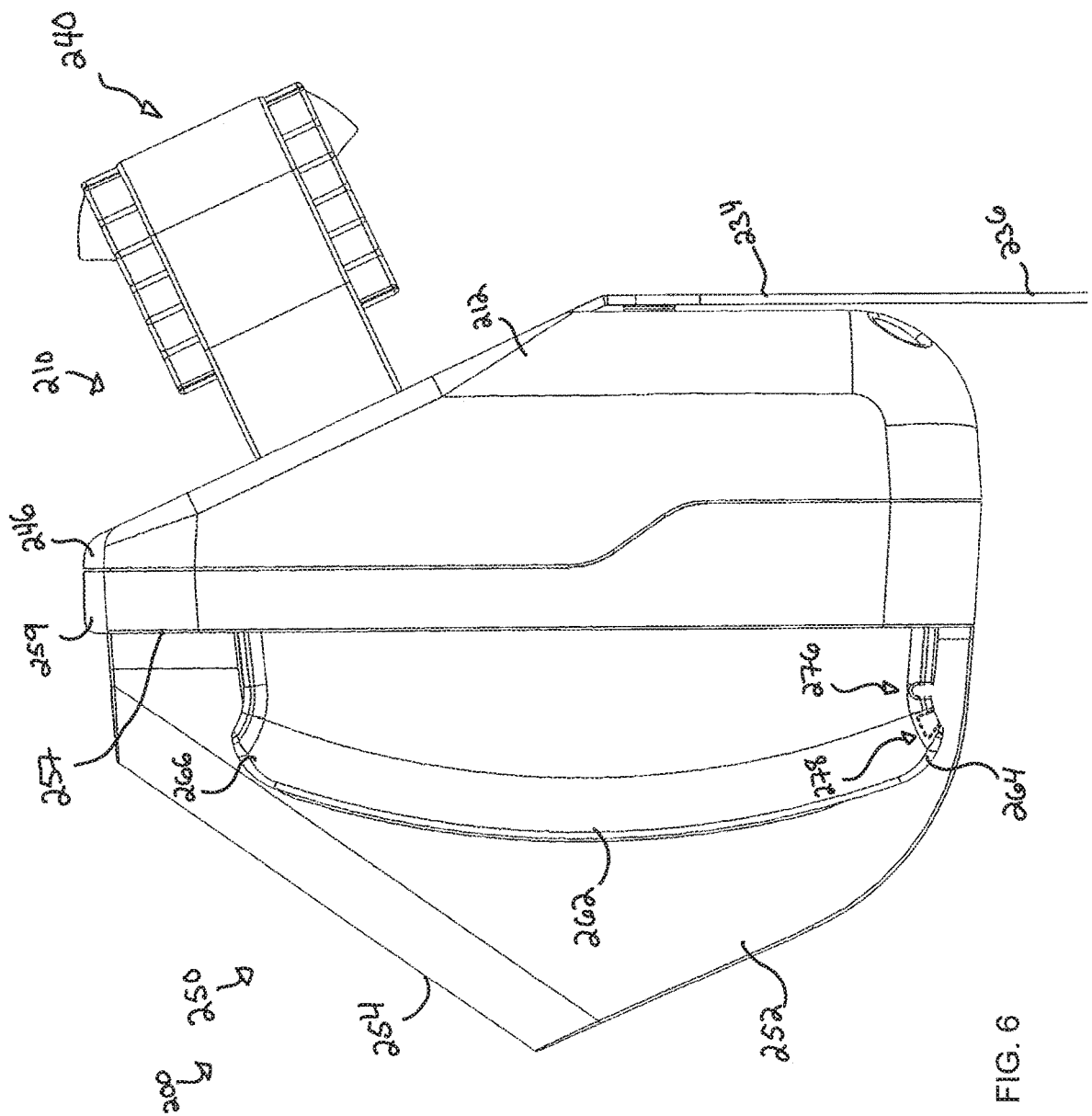
FIG. 6 depicts a side elevational view of the reusable assembly of FIG. 5.
Figure 7:
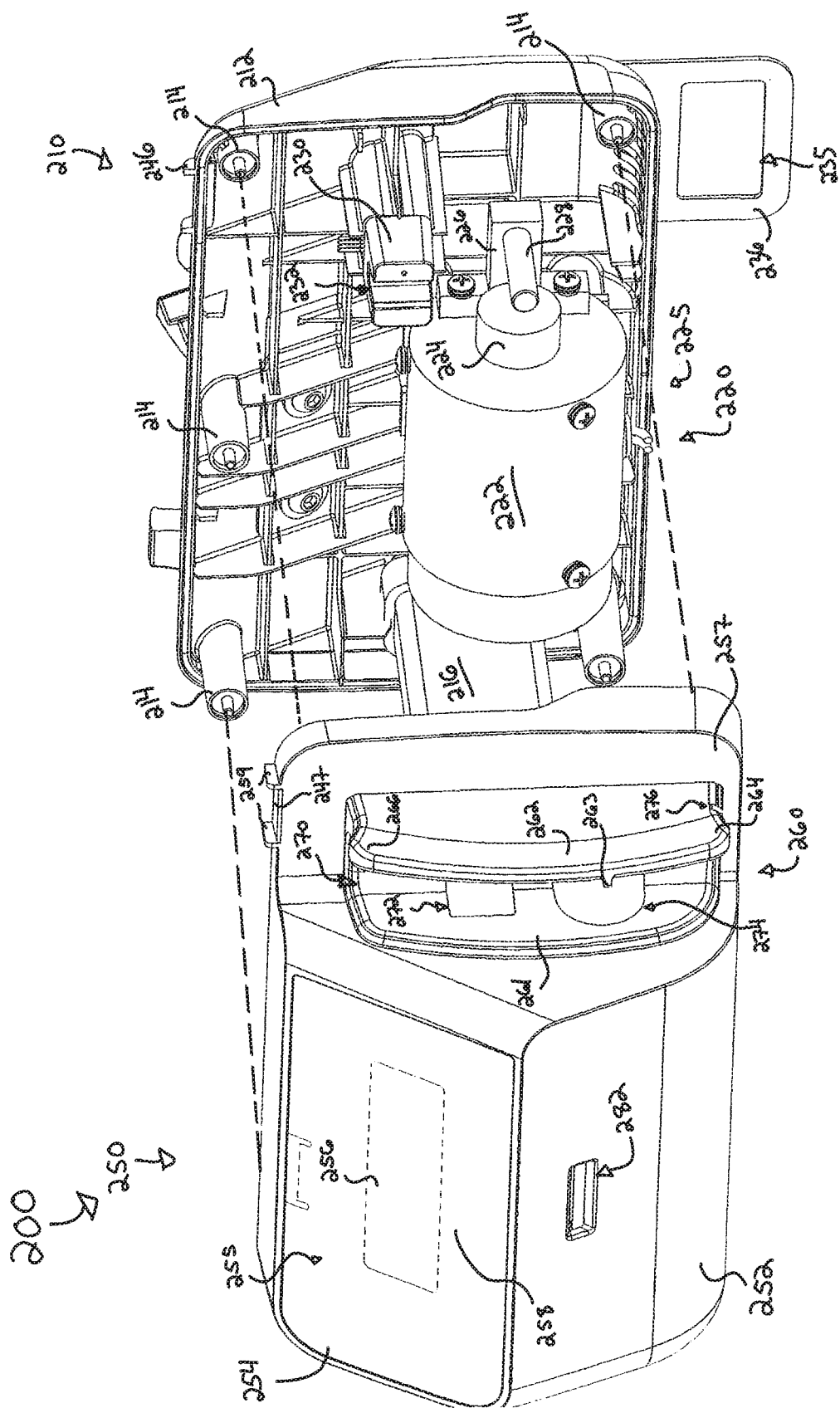
FIG. 7 depicts an exploded perspective view of the reusable assembly of FIG. 5.
Figure 8:
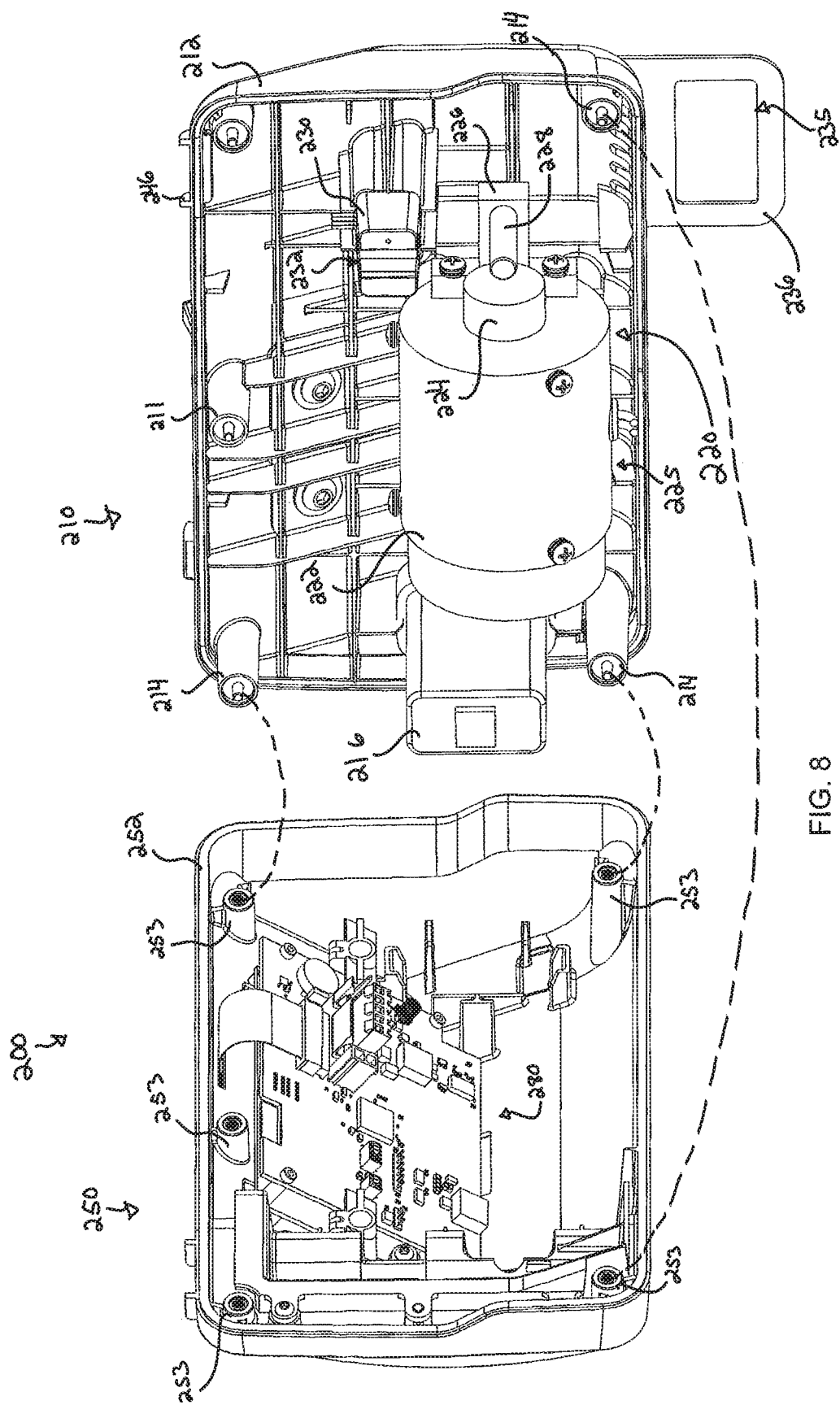
FIG. 8 depicts another exploded perspective view of the reusable assembly of FIG. 5.
Figure 9:
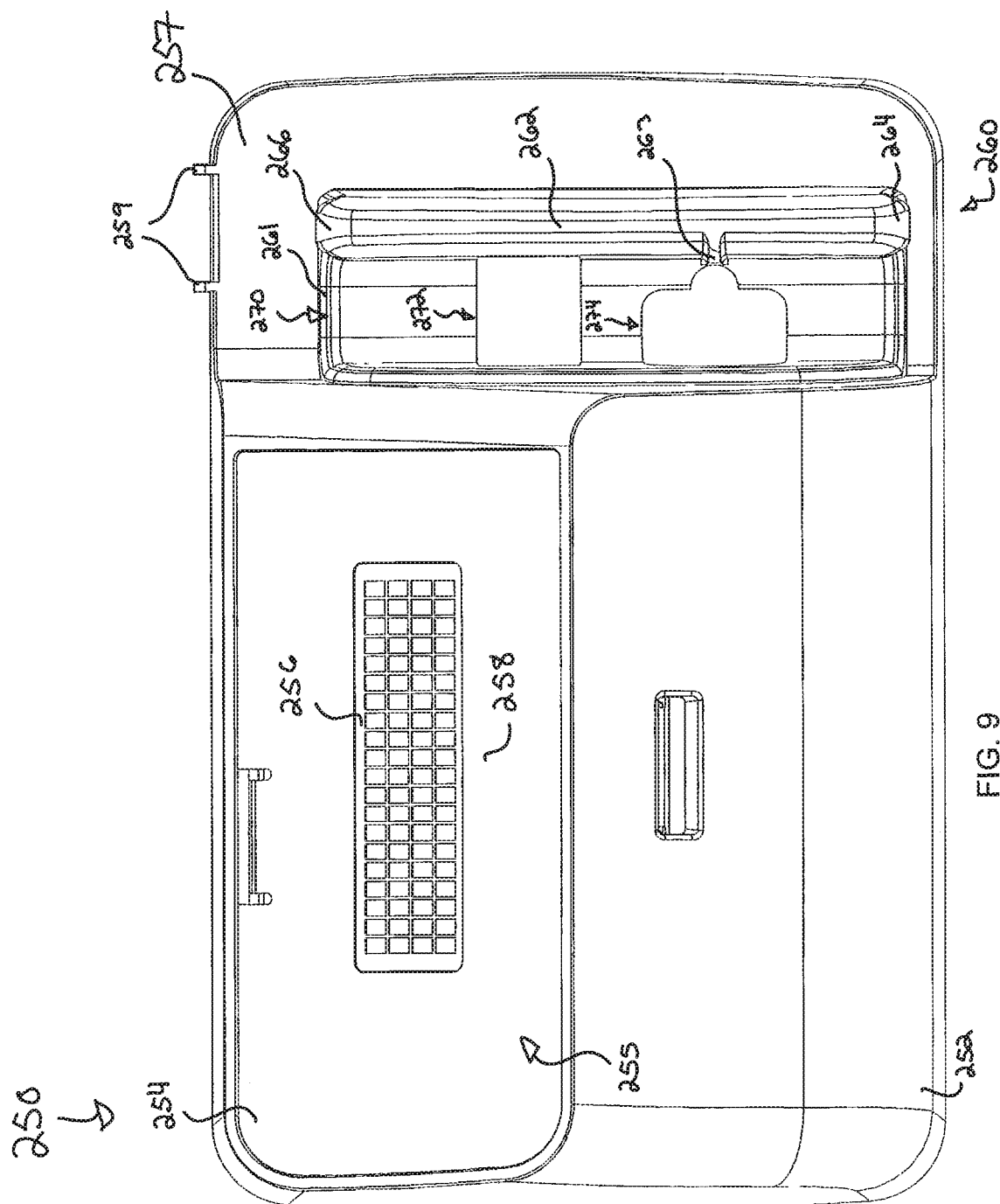
FIG. 9 depicts a front elevational view of a proximal assembly of the reusable assembly of FIG. 5.
Figure 10:
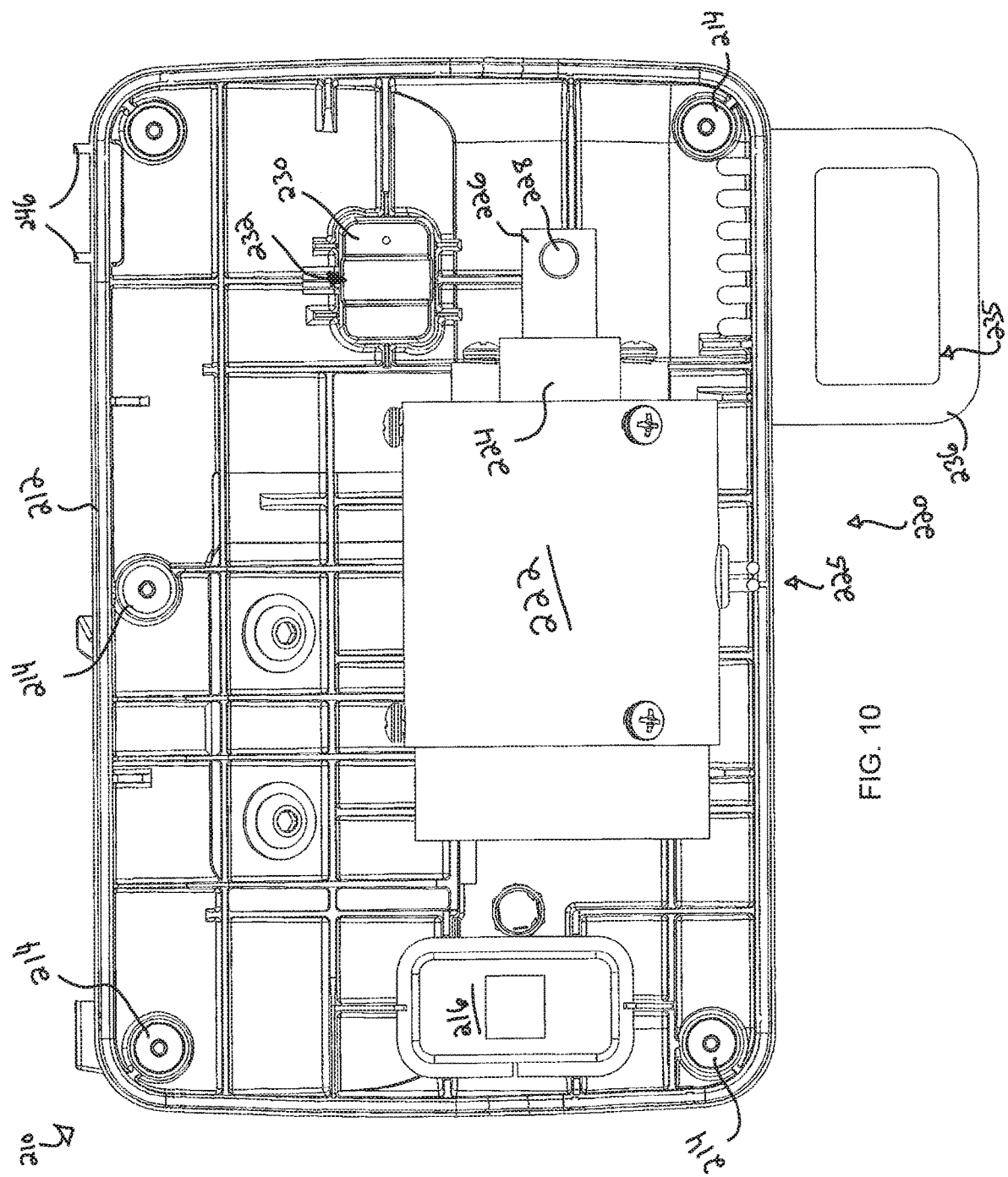
FIG. 10 depicts a front elevational view of a distal assembly of the reusable assembly of FIG. 5.

FIGS. 2-4 show fluid output measuring device (100). As mentioned above, fluid output measuring device (100) includes reusable assembly (200) and disposable assembly (300). As will be described in greater detail below, disposable assembly (300) is selectively attachable to reusable assembly (200) such that disposable assembly (300) may be used a limited number of sessions, such as one, while reusable assembly (200) may be used for more sessions. Disposable assembly (300) is configured to provide fluid communication between input fluid tube (34) and output fluid tube (45), while reusable assembly (200) is configured to manipulate disposable assembly (300) such that disposable assembly (300) selectively accumulates and releases discrete amounts of fluid received from input fluid tube (34) toward output fluid tube (45). Additionally, reusable assembly (200) is configured to store and calculate data corresponding to the volume of each individual discrete amount of fluid stored within disposable assembly (300) prior to releasing the fluid and the time it takes to fill disposable assembly (300) to each discrete volume of fluid.

As best seen in FIGS. 5-8, reusable assembly (200) includes a distal assembly (210) and a proximal assembly (250) that are coupled to each other via respective coupling members (214, 253). Coupling members (214, 253) may attach distal and proximal assemblies (210, 250) through a snap fitting, any variety of mounting features, or any other suitable coupling means that would be apparent to one having ordinary skill in the art in view of the teachings herein. For example, threaded bolts and complementary threading may be used to selectively attach distal assembly (210) with proximal assembly (250). While two assemblies are used in the current example, it should be understood that any suitable number of assemblies may be incorporated to form reusable assembly (200), such as one assembly, three assemblies, or the like.

As best seen in FIGS. 5-9, proximal assembly (250) includes a housing (252) having an exterior portion and an interior portion. The interior portion of housing (252) stores a control assembly (280). Control assembly (280) is in electronic communication with various suitable components of reusable assembly (200) as will be described in greater detail below. Control assembly (280) is configured to receive, store and process data from various suitable components in reusable assembly (200), as well as instruct various suitable components in response to received data. Control assembly (280) is also configured to establish wireless communication with server (50) in order to transfer and/or receive data to/from server (50). Control assembly (280) may have any variety of suitable components as would be apparent to one having ordinary skill in the art. Additionally, control assembly (280) may establish electrical communication with other components of reusable assembly (200) through any suitable means that would be apparent to one having ordinary skill in the art. For instance, control assembly (280) may be connected through other electrical parts via wires stored within the interior of housing (252) or electrical traces embedded into housing (252) or distal assembly (210). While in the current example, it is envisioned that control assembly (280) may establish wireless communication with server (50), any other suitable communication methods may be used as would be apparent to one having ordinary skill in the art in view of the teachings herein, such as wired communication.

The exterior portion of housing (252) includes an upwardly slanted face 54L mounting surface (257) fixed with a disposable mounting assembly (260), and a pair of guide rails (259). Guide rails (259) are spaced apart from each other by a contact wall (247) designed for contact with selected portions of disposable assembly (300) when disposable assembly (300) is selectively attached to reusable assembly (200). As will be described in greater detail below, guide rails (259) align with guide rails (246) of distal assembly (210) in order to provide an insertion path for selected portions of disposable assembly (300) when disposable assembly (300) is selectively attached to reusable assembly (200).

In some instances, it may be difficult for an operator to view graphic user interface (255) if fluid output measuring device (100) is positioned below an operator. An operator may then have to bend or kneel in order to properly view/interact with graphic user interface (255), which may lead to operator discomfort. Therefore, upwardly slanted face (254) includes a graphic user interface (255) in the present example. Upwardly slanted face (254) is angled relative to the rest of housing (252) such that data displayed on graphic user interface (255) may be easily viewed or accessed if fluid output measuring device (100) is positioned below an operator. Therefore, if fluid output measuring device (100) is positioned below the operator, he/she may not have to kneel or bend down in order to read information displayed on graphic user interface (255). Upwardly slanted face (254) may have any suitable angle relative to housing (252) that would be apparent to one having ordinary skill in the art in view of the teachings herein. It should also be understood that upwardly slanted face (254) is merely optional. Therefore, in some instances, housing (252) may not include an upwardly slanted face (254) such that upwardly slanted face may be substantially vertical with respect to housing (252).

Graphic user interface (255) is in communication with control assembly (280) such that graphic user interface (255) may receive data from control assembly (280) as well as send data/commands to control assembly (280). Graphic user interface (255) includes a display (256) and a user input (258). Display (256) is configured to display relative information relating to data collected by, as well as the operation of, fluid output measuring device (100). Examples of such information will be described in greater detail below, while other examples of such information will be apparent to one having ordinary skill in the art in view of the teachings herein. Display (256) may have any suitable components as would be apparent to one having ordinary skill in the art, such as an LCD screen, an array/matrix of character displays, etc. User input (258) is configured to receive instructions from an operator, and transfer those instructions to control assembly (280). User input (258) may include a membrane keypad, a touch screen, a plurality of buttons, or any other suitable means for user input that would be apparent to one having ordinary skill in the art in view of the teachings herein. User input (258) may be configured to receive any suitable number of user instructions that would be apparent to one having ordinary skill in the art in view of the teachings herein. For example, user input (258) may be configured to power on/off fluid output measuring device (100), activate monitoring features of fluid output measuring device (100), scroll through stored data of fluid output measuring device (100), etc.

Housing (252) also defines a memory slot (282). Memory slot 282) may be configured to receive any suitable type of mobile storage device, such as an SD card. Memory slot (282) may receive a mobile storage device such that the mobile storage device is in electrical communication with control assembly (280). Mobile storage device may be able to receive and transfer data to control assembly (280). For example, mobile storage device may be able to connect with control assembly (280) via memory slot (282) in order to provide firmware updates to control assembly (280). Additionally, or alternatively, a mobile storage device may be able to connect with control assembly (280) via memory slot (282) in order to receive monitoring data obtained from proper operation of fluid output measuring device (100). Of course, any other suitable functions of memory slot (282) will be apparent to one having ordinary skill in the art in view of the teachings herein.

As will be described in greater detail below, disposable mounting assembly (260) is configured to selectively receive disposable assembly (300) such that disposable assembly (300) may consistently attach to reusable assembly (200) in substantially the same location relative to reusable assembly (200). Features allowing consistent attachment of disposable assembly (300) relative to reusable assembly (200) may provide greater accuracy of fluid measurements as described in greater detail below.

Disposable mounting assembly (260) includes a u-shaped body (261) extending proximally from mounting surface (257). U-shaped body (261) defines a sensing tube opening (270), a sensor opening (272), and a solenoid opening (274). Sensing tube opening (270) is configured to store portions of a sensing tube (304) of disposable assembly (300) when disposable assembly (300) is properly attached to reusable assembly (200). Sensor opening (272) is dimensioned to receive a fluid level sensor (230) of distal assembly (210) when proximal assembly (250) is properly attached to distal assembly (210). Solenoid opening (274) is dimensioned to receive an actuating member (224) of solenoid assembly (225) when proximal assembly (250) is properly attached to distal assembly (210).

U-shaped body (261) includes an arched projection (262) extending from a downwardly presented nub (264) toward an upwardly presented nub (266). Additionally, arched projection (262) includes a pinch rod support (263) extending inwardly toward sensing tube opening (270) in order to support a pinch rod (228) of distal assembly (210). As will be described in greater detail below, arched projection (262) is configured to receive disposable assembly (300) via an insert opening (308). As will also be described in greater detail below, upwardly presented nub (266) is configured to guide selected portions of disposable assembly (300) during attachment of disposable assembly (300) to reusable assembly (200); while downwardly presented nub (264) defines a cutout (276) and a notch (278) that are configured to mate with selected portions of disposable assembly (300) to help maintain the position of disposable assembly (300) relative to reusable assembly (200) when properly attached.

As best seen in FIGS. 5-8 and FIG. 10, distal assembly (210) includes a housing (212) having an exterior portion and an interior portion. The interior portion of housing (212) houses a battery (216) and a fluid management assembly (220). Battery (216) is configured to power any suitable electrically powered components of fluid output measuring device (100) while disconnected from external sources of electricity, such as a wall outlet. Battery (216) may establish electrical connection with electrically powered components through any suitable means known to one having ordinary skill in the art in view of the teachings herein. For example, battery (216) may connect with electrically powered components through wires housed within housings (212, 252), through electrical traces embedded into housings (212, 252), etc.

As will be described in greater detail below, components of fluid management assembly (220) are configured to selectively collect and release discrete amounts of fluid within disposable assembly (300) based on the amount of fluid collected within disposable assembly (300) from input fluid tube (34) of catheter assembly (30). Additionally, as will be described in greater detail below, fluid management assembly (220) is also configured to communicate data to control assembly (280) representing the volume of fluid collected within disposable assembly (300) prior to releasing the fluid. Control assembly (280) may also measure the time it takes for fluid management assembly (220) to collect and release each discrete accumulation of fluid within disposable assembly (300).

Fluid management assembly (220) includes a solenoid assembly (225), a mounting bracket (226), a pinch rod (228), and a fluid level sensor (230). Solenoid assembly (225) includes a static member (222) fixed to housing (212), and an actuating member (224) slidably attached to static member (222). Static member (222) is configured to linearly drive actuating member (224) toward and away from pinch rod (228) in response to instructions from control assembly (280). Mounting bracket (226) is fixed relative to static member (222) while pinch rod (228) proximally extends from mounting bracket (226). Pinch rod (228) extends through solenoid opening (274) while actuating member (224) may translate through solenoid opening (274) when proximal assembly (250) and distal assembly (210) are properly attached.

Figure 24A:
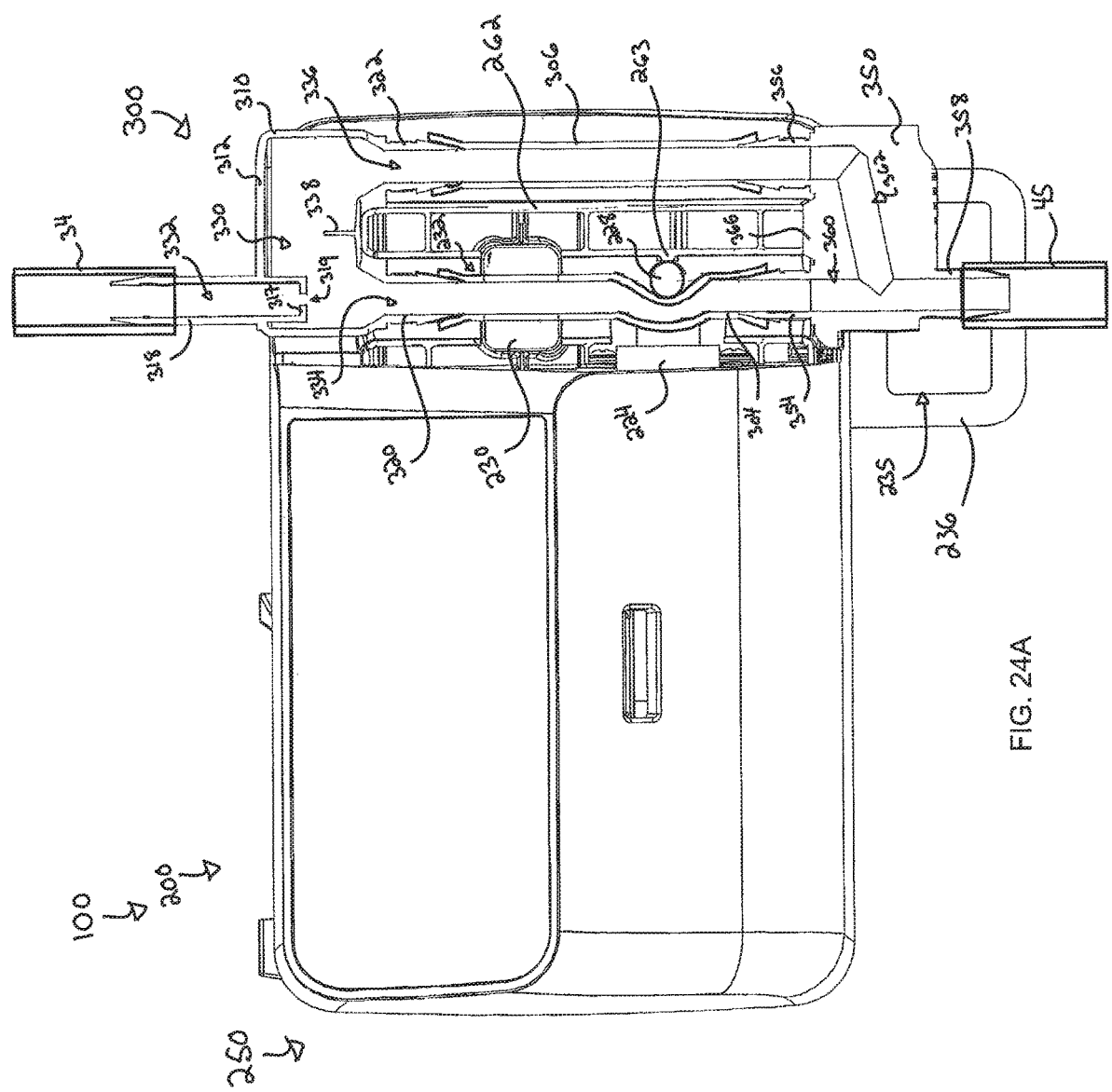
FIG. 24A depicts a partial cross-sectional front view of the fluid output measuring device of FIG. 2 in an open configuration, taken along line 24-24 of FIG. 2.
Figure 24B:
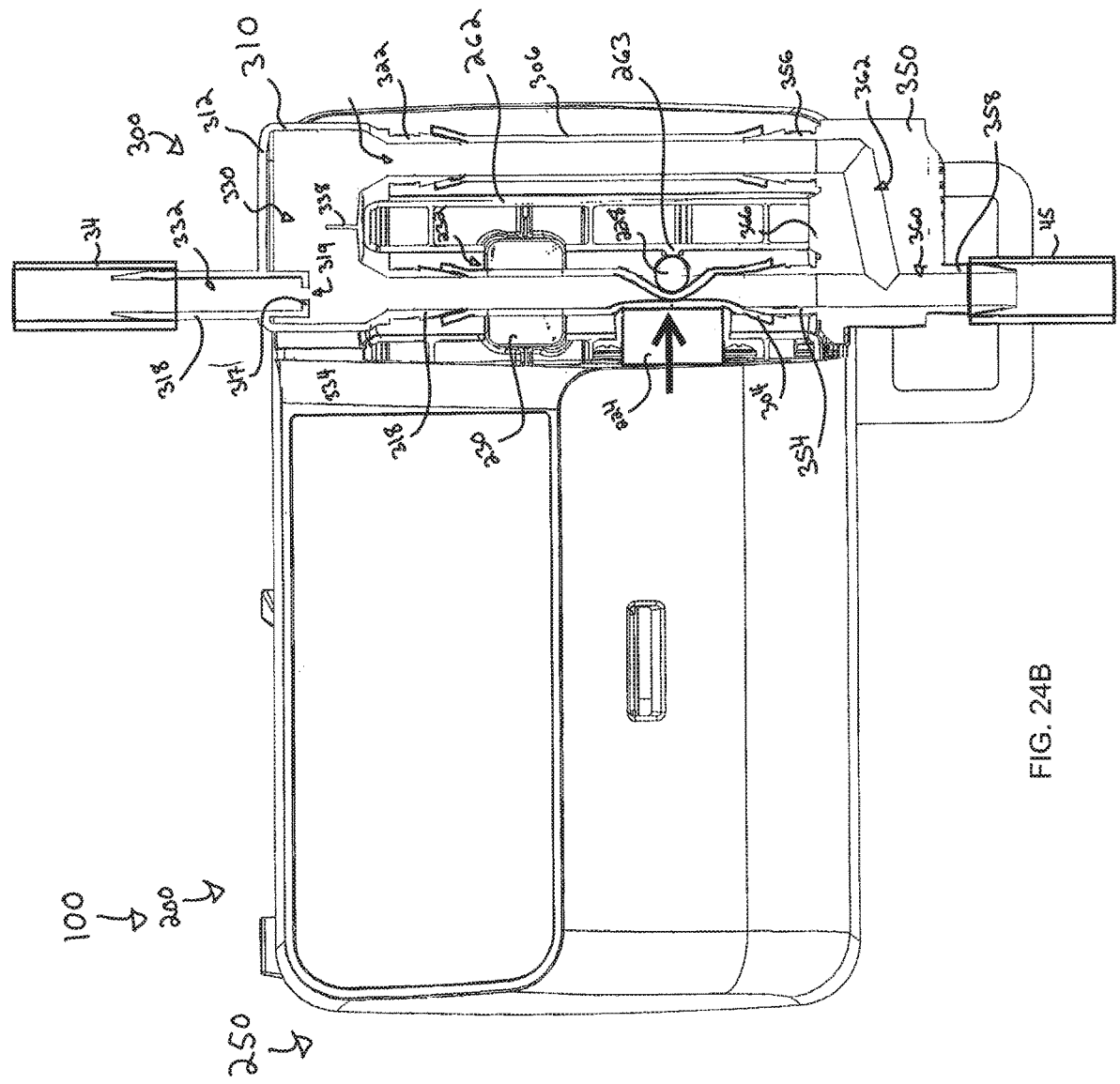
FIG. 24B depicts a partial cross-sectional front view of the fluid output measuring device of FIG. 2 in a closed configuration, taken along line 24-24 of FIG. 2.
Figure 24C:
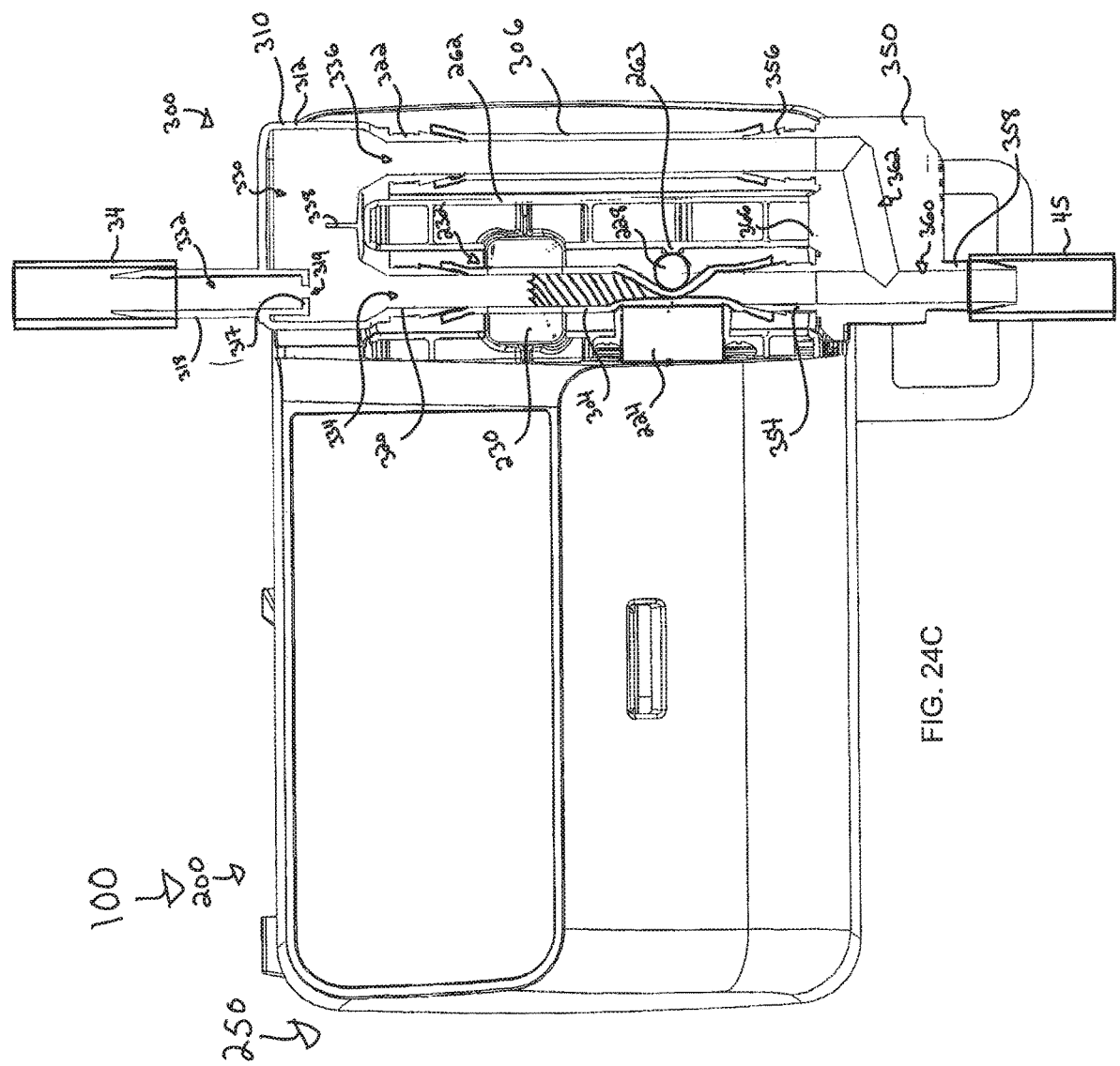
FIG. 24C depicts a partial cross-sectional front view of the fluid output measuring device of FIG. 2 in the closed configuration where the disposable assembly of FIG. 11 is partially filled with fluid, taken along line 24-24 of FIG. 2.
Figure 24D:
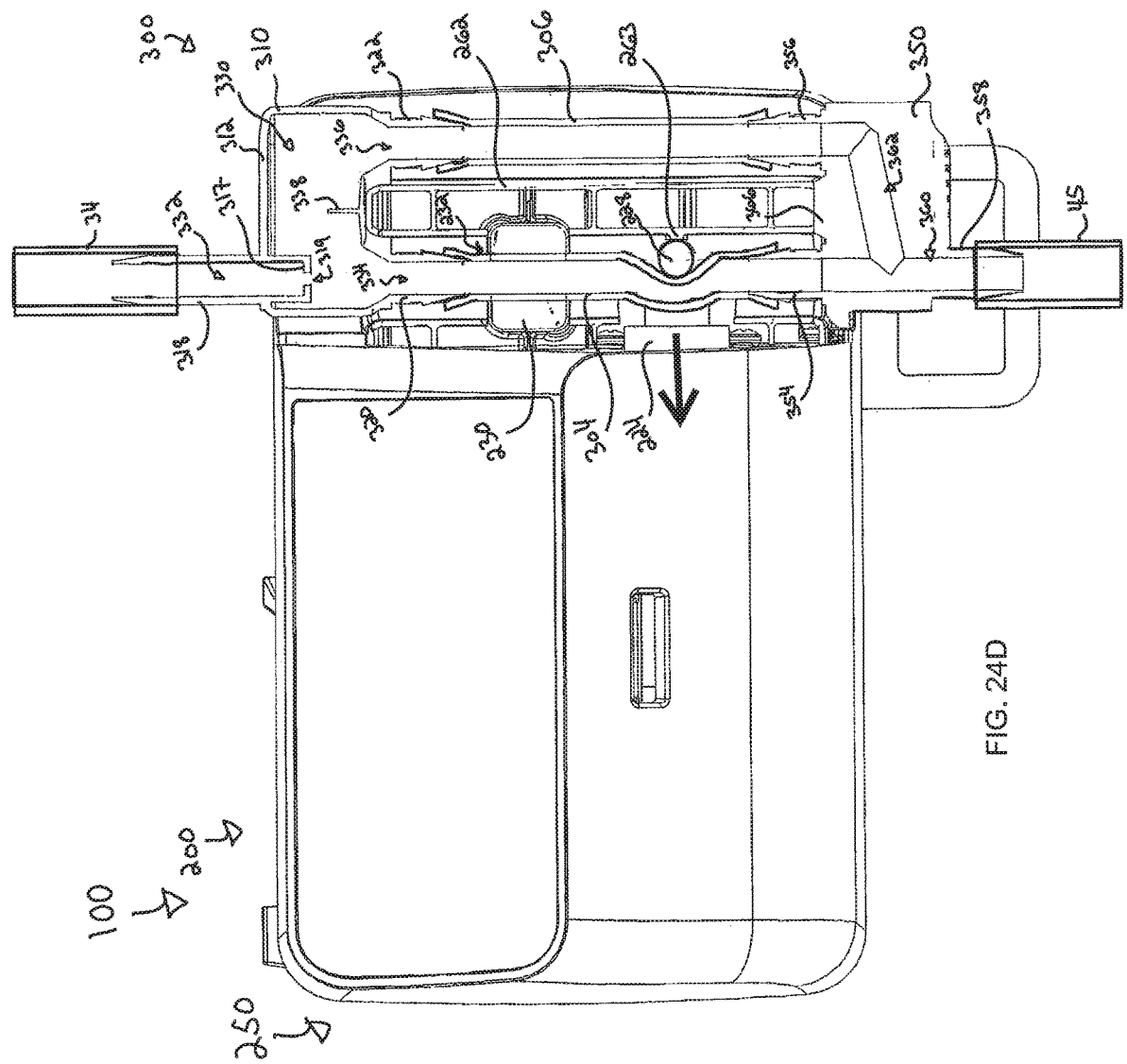
FIG. 24D depicts a partial cross-sectional front view of the fluid output measuring device of FIG. 2 transitioned from the closed configuration to the open configuration in order to drain fluid partially filled within the disposable assembly of FIG. 11.

As will be described in greater detail below, movement of actuating member (224) toward and away from pinch rod (228) may act as a pinch valve to disposable assembly (300) when properly attached, controlling when certain portions of disposable assembly (300) collect or release fluid. In particular, disposable assembly (300) may collect fluid when actuating member (224) is in a closed position (as shown in FIGS. 24B-24C) relative to pinch rod (228) and release fluid when actuating member (224) is in an open position (as shown in FIG. 24A and FIG. 24D) relative to pinch rod (228). Therefore, control assembly (280) may determine when disposable assembly (300) collects fluid or releases fluid based on the placement of actuating member (224) relative to pinch rod (228).

Solenoid assembly (225) may include any suitable components known to one having ordinary skill in the art in view of the teachings herein. While in the current example, solenoid assembly (225) is used to actuate toward and away from pinch rod (228), any other suitable actuating mechanism may be utilized as would be apparent to one having ordinary skill in the art in view of the teachings herein. For example, a motor, lead screw, and bolt may be incorporated into fluid management assembly (220) in replacement of solenoid assembly (225).

Fluid level sensor (230) is fixed relative to housing (212) and extends through sensor opening (272) when distal assembly (210) is properly attached to proximal assembly (250). Therefore, fluid level sensor (230) is also fixed relative to pinch rod (228). Fluid level sensor (230) defines a sensing tube channel (232) dimensioned to receive sensing tube (304) of disposable assembly (300). In the current example, fluid level sensor (230) is an ultrasonic sensor. However, any suitable sensor may be used as would be apparent to one having ordinary skill in the art in view of the teachings herein. As mentioned above and as will be described in greater detail below, disposable assembly (300) is configured to attach to reusable assembly (200) in such a way that disposable assembly (300) attaches to reusable assembly (200) uniformly in substantially the same orientation. Therefore, the distance of sensing tube (304) between pinch rod (228) fluid level sensor (230) may be substantially uniform.

As will also be described in greater detail below, sensing tube (304) is configured to collect fluid when actuating member (224) is translated toward pinch rod (228) in the closed position such that collected fluid accumulates toward fluid level sensor (230). Once fluid fills within sensing tube (304) adjacent to and within the confines of sensing tube channel (232), fluid level sensor (230) may send a signal to control assembly (280) correlating to fluid being filled to a certain vertical level within sensing tube channel (232), which control assembly (280) may store. Control assembly (280) may then send a signal to solenoid assembly (225) to drive actuating member (224) away from pinch rod (228) to the open position such that accumulated fluid is released from sensing tube (304). In other words, control assembly (280) may send a signal to solenoid assembly (225) to open pinch valve. Because the distance of sensing tube (304) between pinch rod (228) and fluid level sensor (230) may be substantially uniform, and fluid level sensor (230) sends a signal to control assembly (280) corresponding to the level at which fluid was filled within sensing tube channel (232) of fluid level sensor (230), the signal corresponding to the level at which fluid was filled within sensing tube channel (232) may correspond with a specific volume of fluid accumulated within sensing tube (304). Control assembly (280) may also store the amount of time it took to fill sensing tube (304) and the volume of fluid within sensing tube (304) for further analysis, as described as below.

The exterior portion of housing (212) includes guide rails (246) spaced apart between a slanted wall (249), a collection bag plate (234), a clamp assembly (240), and an external power connection (248). As will be described in greater detail below, slanted wall (249) may help couple selected portions of reusable assembly (300) with disposable assembly (200). Collection bag plate (234) is fixed to housing (212) and includes a downwardly extending arm (236) defining a coupling hole (235). Coupling hole (235) is configured to receive a coupling portion of collection bag (340) or any other suitable fluid collection means. Coupling hole (235) is located on downwardly extending arm (236) relatively close to the rest of fluid output measuring device (100) so that collection bag (340) may be relatively close to measuring device (100).

Clamp arm assembly (240) is configured to allow an operator to selectively fix fluid output measuring device (100) to any suitable structure, such as an IV pole or rail (22) on bed assembly (20). Clamp arm assembly (240) includes an actuating member (242) movably coupled to a static member (244). Static member (244) is fixed to housing (212) such that movement of actuating member (242) toward static member (244) may provide a frictional breaking force against the desired mounting structure so that fluid output measuring device (100) does not easily move relative to the mounting structure. In the current example, actuating member is threadably coupled to static member (244) such that rotation of actuating member (242) causes linear translation of actuating member (242) relative to static member (244). Clamp assembly (240) may comprise a plurality of ridges to further increase the frictional breaking force described above. While in the current example, actuating member (242) is threadably coupled with static member (244), any other suitable coupling may be used as would be apparent to one having ordinary skill in the art.

External power connection (248) is configured to couple to an external power source such that the external power source may power fluid output measuring device (100) and/or charge battery (216). Therefore, fluid output measuring device (100) may be powered by an external power source, battery (216), or both. External power connection (248) may contain any suitable components that would be apparent to one having ordinary skill in the art in view of the teachings herein.

FIGS. 11-22 show disposable assembly (300) and its various components. As will be described in greater detail below, disposable assembly (300) is configured to provide fluid communication between input fluid tube (34) and output fluid tube (45). As described above and as will be described in greater detail below, disposable assembly (300) has various features to consistently attach to reusable assembly (200) in substantially the same location relative to reusable assembly (200). These features may provide greater accuracy of fluid measurements as described above, and described in greater detail below.

As best seen in FIGS. 11-14, disposable assembly (300) includes a fluid input fitting (310), a sensing tube (304), a bypass tube (306), a fluid output fitting (350), and a vent (302) in fluid communication with fluid input fitting (310). Fluid input fitting (310) is configured to couple with input fluid tube (34) while fluid output fitting (350) is configured to couple with output fluid tube (345). Therefore, fluid from catheter (32) may travel through input fluid tube (34) and into disposable assembly (300) via fluid input fitting (310). Once fluid travels through disposable assembly (300), fluid may exit disposable assembly (300) via fluid output fitting (350) toward output fluid tube (45) and collection bag (40).

Fluid input fitting (310) includes a body (312), a distally presented resilient arm (314) terminating in a downwardly presented protrusion (316), a flow regulating input barb fitting (318) extending upwardly from body (312), a sensing barb fitting (320) extending downwardly from body (312), a bypass barb fitting (322) extending downwardly from body (312) and laterally offset from sensing barb fitting (320), and a vent connection (326) extending from a portion of flow regulating input barb fitting (318) located above body (312).

As will be described in greater detail below, distally presented resilient arm (314) is configured to be inserted between pairs of guide rails (246, 259) to abut against contact wall (247) in order to further guide insertion of disposable assembly (300) toward reusable assembly (200). Resilient arm (314) may further indicate the orientation at which disposable assembly (300) should be oriented. A pair of contact ribs (324) extend distally from body (312) and are configured to make flush contact against mounting surface (257) of reusable assembly (200) when disposable assembly (300) is properly attached to reusable assembly (200). A pair of arched guide members (328) extend toward each other from sensing barb fitting (320) and bypass barb fitting (322), respectively. As will be described in greater detail below, arched guide members (328) are configured to rest on top of upwardly presented nub (266) when disposable assembly (300) is being attached to reusable assembly (200) in order to further guide disposable assembly (300) toward reusable assembly (200).

Figure 18:
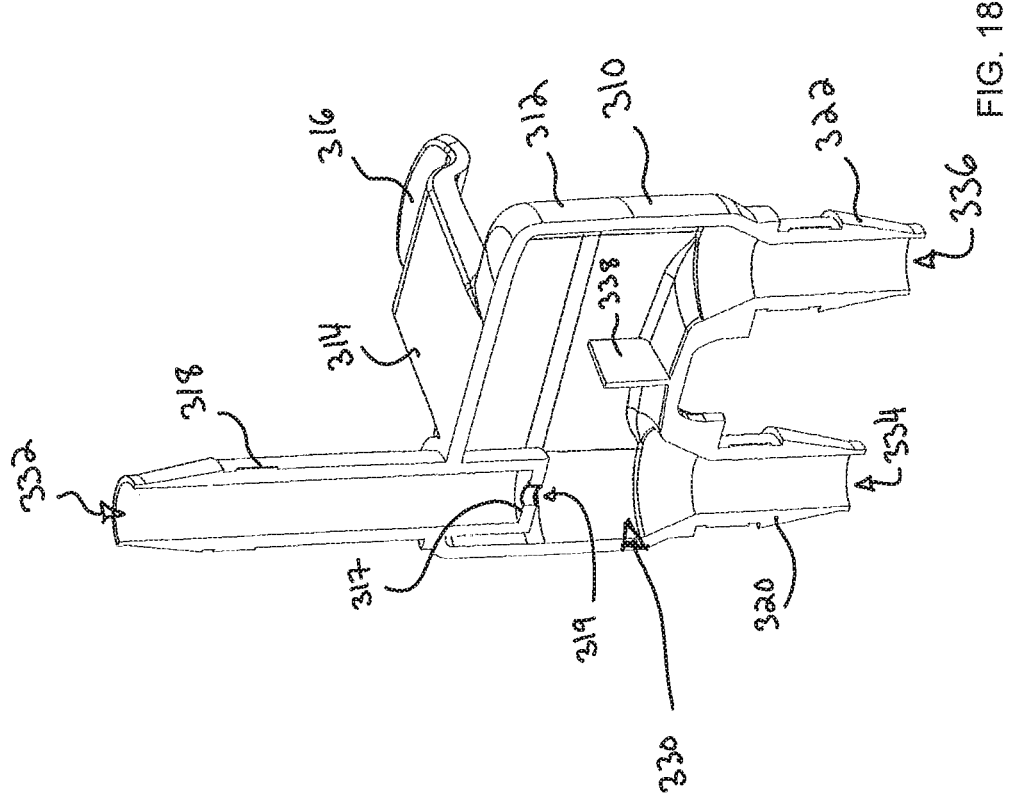
FIG. 18 depicts cross-sectional perspective view of the fluid input fitting of FIG. 15, taken along line 18-18 of FIG. 15.
Figure 19:
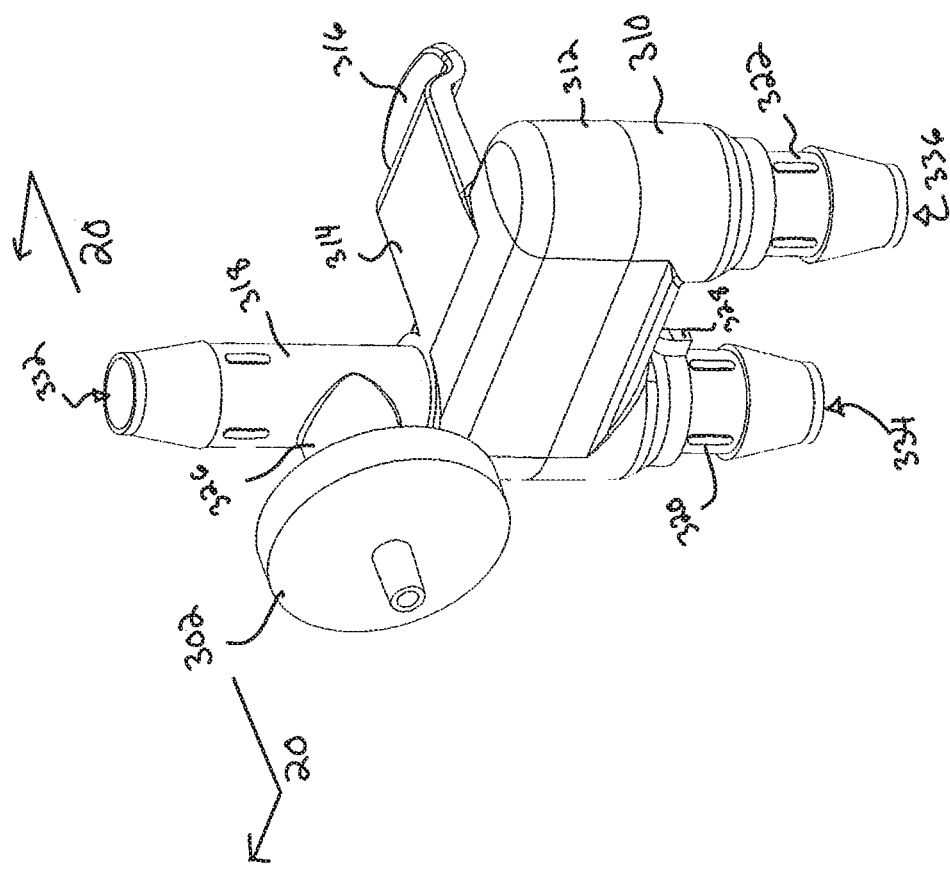
FIG. 19 depicts a perspective view of the fluid input fitting of FIG. 15 attached to a vent of the disposable assembly of FIG. 11.
Figure 20:
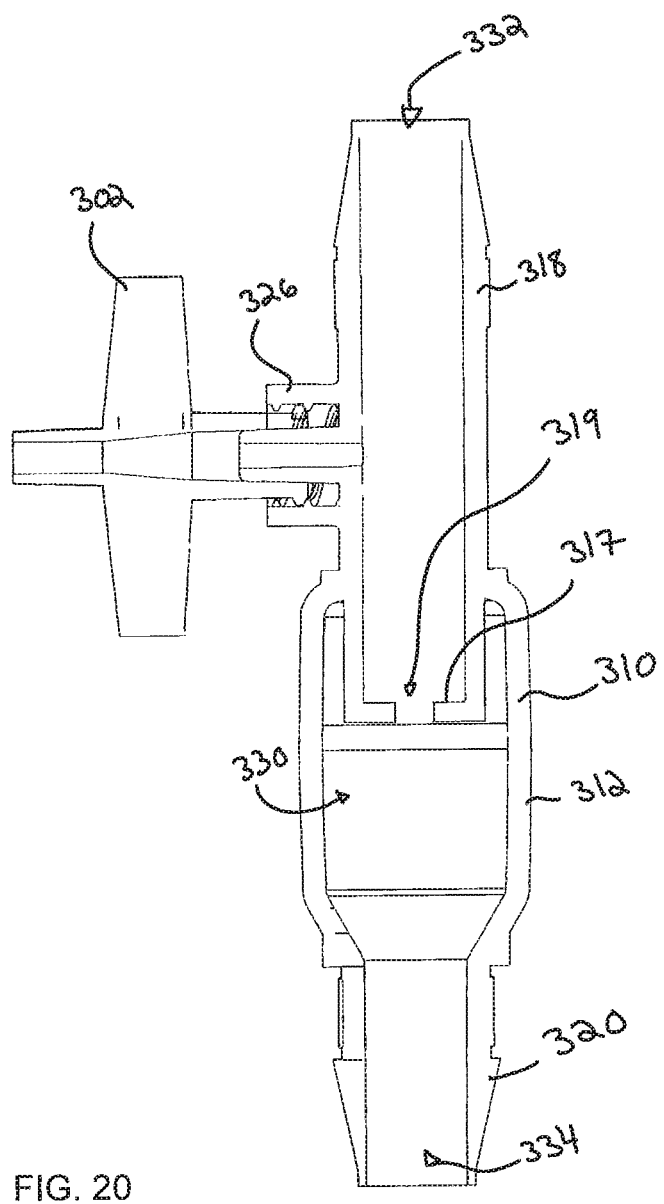
FIG. 20 depicts a cross-sectional side view of the fluid input fitting of FIG. 15 attached to the vent of FIG. 19, taken along line 20-20 of FIG. 19.

Flow regulating barb fitting (318) is configured to couple with input fluid tube (34) via an interference fit to provide a fluid tight connection between fluid input fitting (310) and input fluid tube (34). While an interference fit is used to connect fluid input fitting (310) and input fluid tube (34), any other suitable connection may be used as would be apparent to one having ordinary skill in the art in view of teachings herein, such as a leer fitting or adhesives. As best seen in FIG. 18, flow regulating barb fitting (318) defines a flow regulator input channel (332). As best seen in FIG. 20, vent connection (326) connects with vent (302) to provide fluid communication between an external portion of disposable assembly (300) and flow regulator input channel (332). Vent (302) may help release pressure buildup within flow regulator input channel (332). Vent (302) may be a bacterial air vent.

Flow regulator input channel (332) terminates at a bottom wall (317) that defines a flow regulating orifice (319). Flow regulating orifice (319), in combination with vent (302), is configured to normalize the flow of fluid to a fixed maximum rate between flow regulator input channel (332) and a fluid chamber (330) defined by body (312). This may help produce highly precise fluid measurements within sensing tube (304). Flow regulating orifice (319) may be especially important during a "bolus" event, which is when a larger-than-normal amount of fluid (i.e., a bolus of fluid) is passed through input fluid tube (34) into disposable assembly (300) within a substantially short time frame. Flow regulating orifice (319) is dimensioned by bottom wall (317) with a specific cross-sectional geometry, area, and vertical depth. Flow regulating orifice (319) may be located at a specific distance from vent (302) in order to induce laminar flow of fluid through flow regulating orifice (319) upon the occurrence of any bolus effect. Therefore, flow regulating orifice (319) and vent (302) may help prevent turbulent flow of fluid.

In the current example, the specific cross-sectional geometry of flow regulating orifice (319) is circular with a 7.94 mm diameter, having a cross-sectional area of 50 mm$^2$. The depth/thickness of bottom wall (317) is 1.4 mm. Also, in the current example, vent (302) has a diameter of 3 mm with a cross-sectional area of 7.1 mm$^2$, while the distance between the top of bottom wall (317) and the center of vent connection (326) is 19.30 mm. It should be understood that these dimensions are merely illustrative examples and that they are not intended to limit the scope of the invention.

While the current example has one vent (302), and bottom wall (317) defines one flow regulating orifice (319) in a circular cross-sectional geometry, any other suitable number of flow regulating orifices (319) with any other suitable cross-sectional geometry may be used. For example, a multitude of orifices and a series of bacterial air vents may be used. Orifices may have rectangular cross-sectional geometries, matching cross-sectional geometries, different cross-sectional geometries, uniform depths, different depths, etc. Orifices may be located on the side walls of flow regulating barb fitting (318) terminating within fluid chamber (330). Orifice may be a smaller tube within flow regulating barb fitting (318) and extend into fluid chamber (330). Orifice may be a chicane design within fluid input fitting (310) having a spiral design or a series of 180 degree turns. Any other suitable orifices may be used that would be apparent to one having ordinary skill in the art in view of the teachings herein.

Sensing barb fitting (320) is configured to couple with sensing tube (304) via an interference fit to provide a fluid tight connection between fluid input fitting (310) and sensing tube (304). While an interference fit is used to connect fluid input fitting (310) and sensing tube (304), any other suitable connection may be used that would be apparent to one having ordinary skill in the art in view of the teachings herein, such as a luer fitting or adhesives. As best seen in FIG. 18, sensing barb fitting (320) defines an output channel (334). As mentioned above, body (312) also defines a fluid chamber (330) configured to receive fluid from flow regulator input channel (332). Flow regulating orifice (319) may be directly above, or approximately above output channel (334). Therefore, fluid may flow through flow regulator input channel (322), flow regulating orifice (319), fluid chamber (330), and output channel (334) into sensing tube (304).

Overflow barb fitting (322) is configured to couple with overflow tube (306) via an interference fit to provide a fluid tight connection between fluid input fitting (310) and overflow tube (306). While an interference fit is used to connect fluid input fitting (310) and overflow tube (306), any other suitable connection may be used that would be apparent to one having ordinary skill in the art in view of the teachings herein, such as a luer fitting or adhesives. As best seen in FIG. 18, overflow barb fitting (322) defines an overflow channel (336). Additionally, an overflow wall (338) extends upwardly from a bottom portion of fluid chamber (330) located between output channel (334) and overflow channel (336). If, for some reason, fluid can no longer travel through output channel (334) into sensing tube (304), fluid may travel over overflow wall (338), through overflow channel (336), and within overflow tube (306). This may prevent fluid backup within fluid chamber and flow regulator input channel (332).

Figure 21:
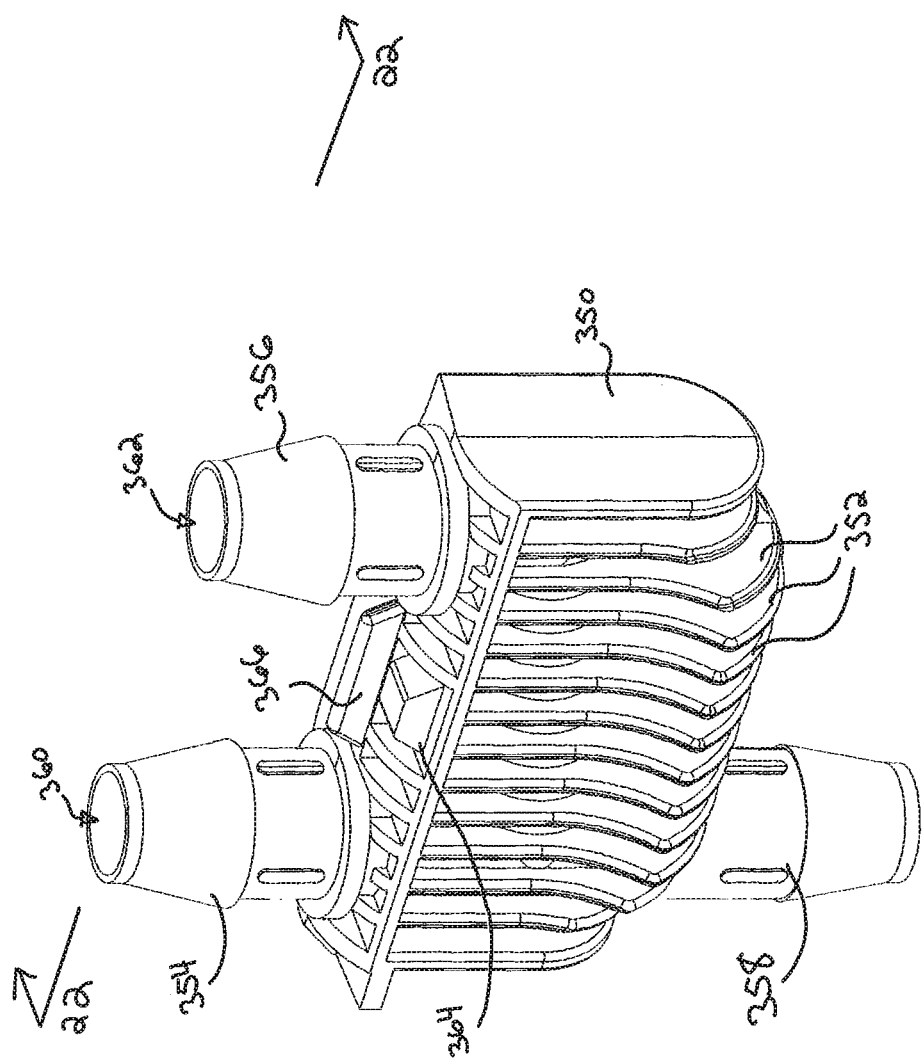
FIG. 21 depicts a perspective view of a fluid output fitting of the disposable assembly of FIG. 11.

FIGS. 21-22 show fluid output fitting (350). Fluid output fitting (350) is configured to provide fluid communication between sensing tube (304) and output fluid tube (45), as well as provide fluid communication between bypass tube (306) and output fluid tube (45). Therefore, fluid may travel through either sensing tube (304) or bypass tube (306), through fluid output fitting (350), output fluid tube (45), and into collection bag (40).

Fluid output fitting (350) includes a plurality of gripping ribs (352), a sensing barb fitting (354), a bypass barb fitting (356), a bottom barb fitting (358), and a protrusion (366) and resilient tab (366) both extending upwardly from gripping ribs (352). Gripping ribs (352) extend from the bottom of both sensing barb fitting (354) and bypass barb fitting (356) toward the top of bottom barb fitting (358). Gripping ribs (352) allow for an operator to better grip disposable assembly (300) while attached disposable assembly (300) to reusable assembly (200), as will be described in greater detail below.

As best seen in FIG. 22, sensing barb fitting (354) and bottom barb fitting (358) together define an output channel (360), while bypass barb fitting (356) defines an overflow channel (362) in fluid communication with output channel (360).

Sensing barb fitting (354) is configured to couple with sensing tube (304) via an interference fit to provide a fluid tight connection between fluid output fitting (350) and sensing tube (304). While an interference fit is used to connect fluid output fitting (350) and sensing tube (304), any other suitable connection may be used that would be apparent to one having ordinary skill in the art in view of the teachings herein, such as a leer fitting or adhesives. Therefore, sensing bar fitting (354) may couple with sensing tube (304) such that fluid may flow from the bottom of sensing tube (304) into output channel (360).

Bottom bar fitting (358) is configured to couple with output fluid tube (45) via an interference fit to provide a fluid tight connection between fluid output fitting (350) and output fluid tube (45). While an interference fit is used to connect fluid output fitting (350) and output fluid tube (45), any other suitable connection may be used that would be apparent to one having ordinary skill in the art in view of the teachings herein, such as a leer fitting or adhesives. Therefore, output fluid tube (45) may couple with bottom barb fitting (358) such that fluid may flow through output channel (360), into output fluid tube (45), and into collection bag (40).

Bypass barb fitting (356) is configured to couple with bypass tube (306) via an interference fit to provide a fluid tight connection between fluid output fitting (350) and bypass tube (306). While an interference fit is used to connect fluid output fitting (350) and bypass tube (306), any other suitable connection may be used that would be apparent to one having ordinary skill in the art in view of the teachings herein, such as a leer fitting or adhesives. Therefore, bypass tube (306) may couple with bypass barb fitting (356) such that fluid may flow through bypass tube (306), overflow channel (362), output channel (360), output fluid tube (45), and into collection bag (40).

Figure 11:
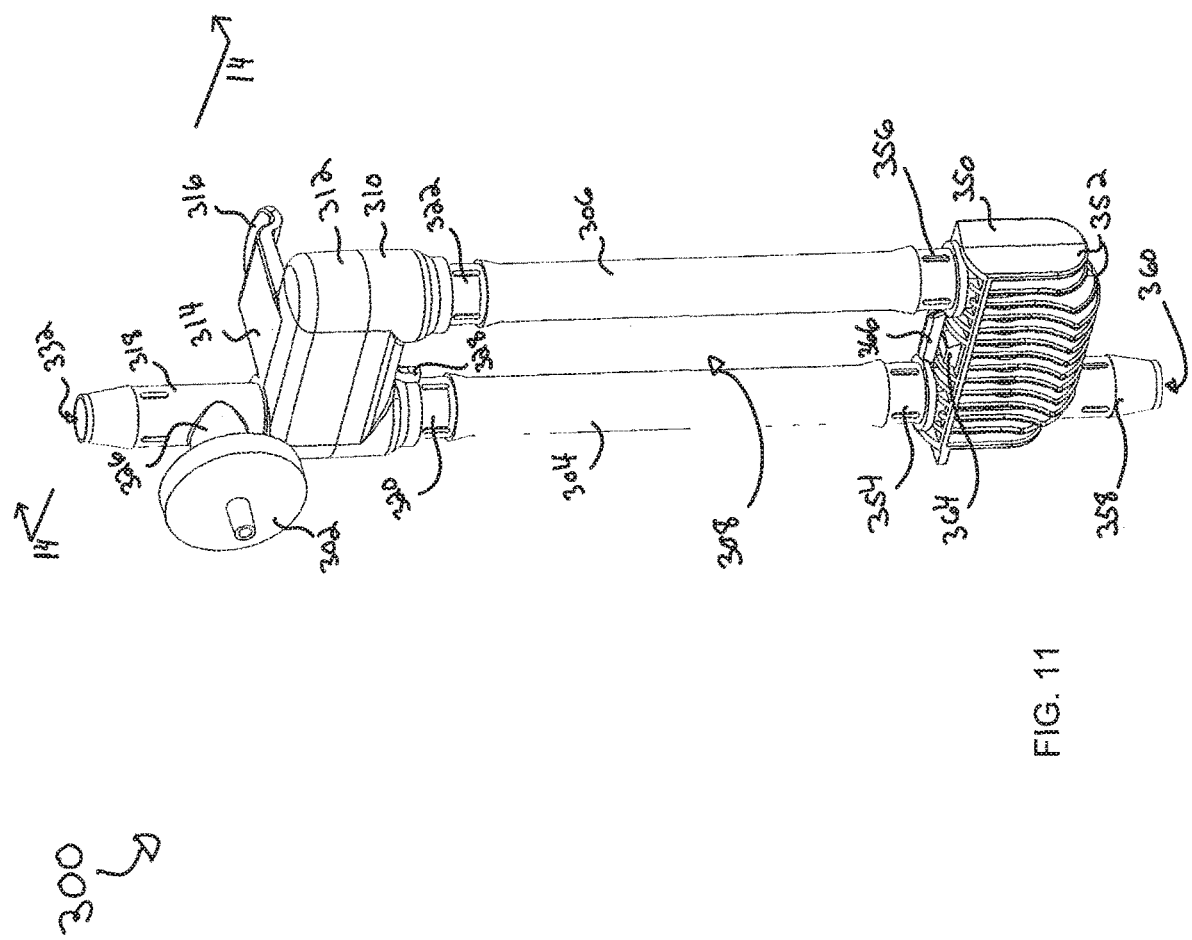
FIG. 11 depicts a perspective view of a disposable assembly of the fluid output measuring device of FIG. 2.
Figure 12:
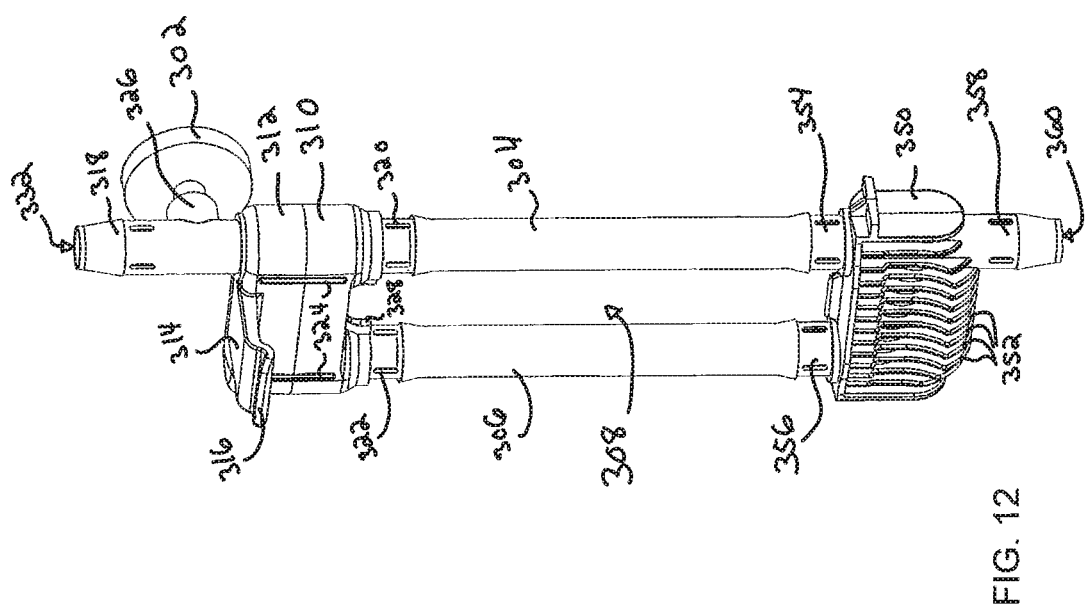
FIG. 12 depicts another perspective view of the disposable assembly of FIG. 11.
Figure 13:
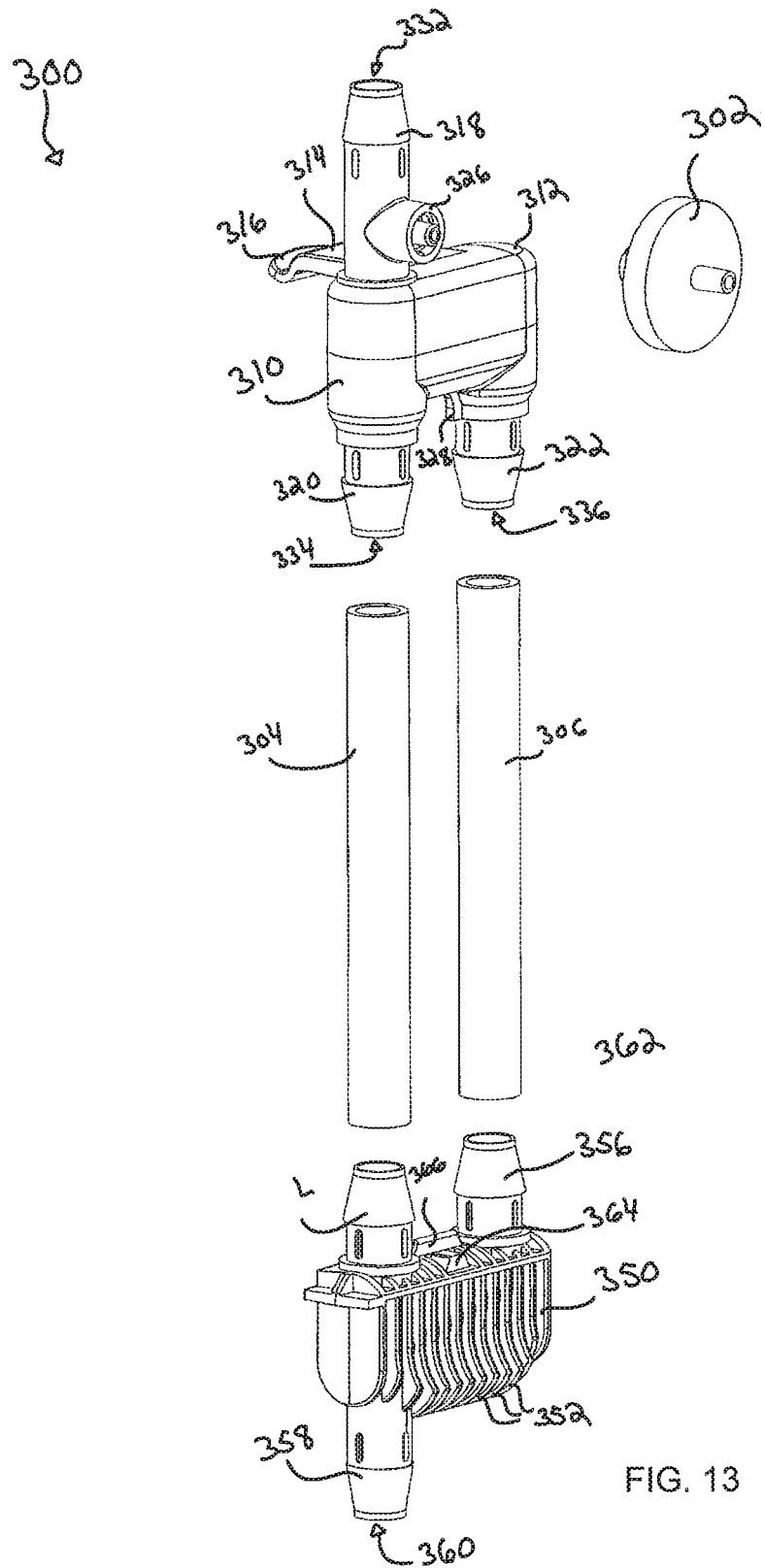
FIG. 13 depicts an exploded perspective view of the disposable assembly of FIG. 11.
Figure 14:
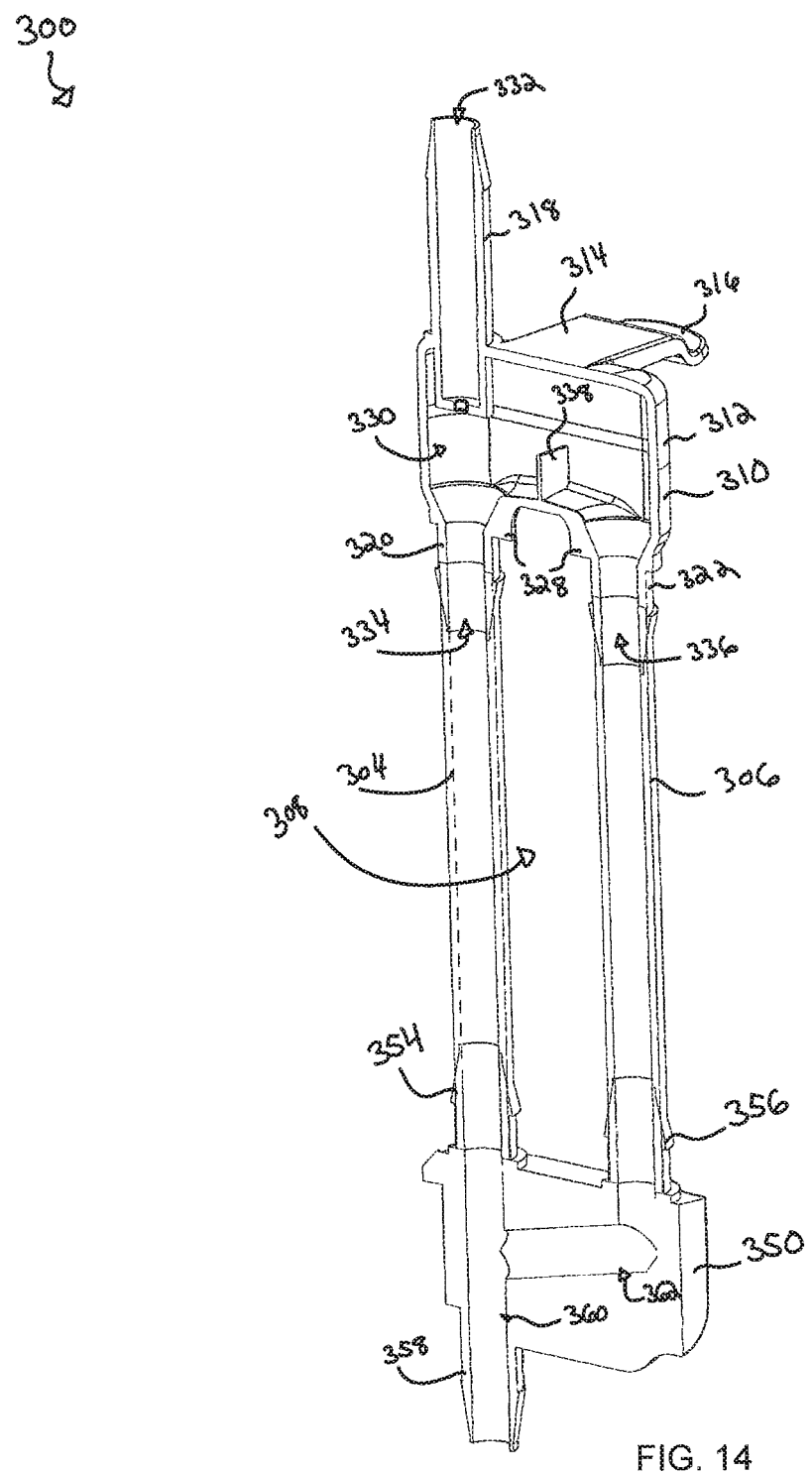
FIG. 14 depicts a cross-sectional perspective view of the disposable assembly of FIG. 11, taken along line 14-14 of FIG. 11.
Figure 15:
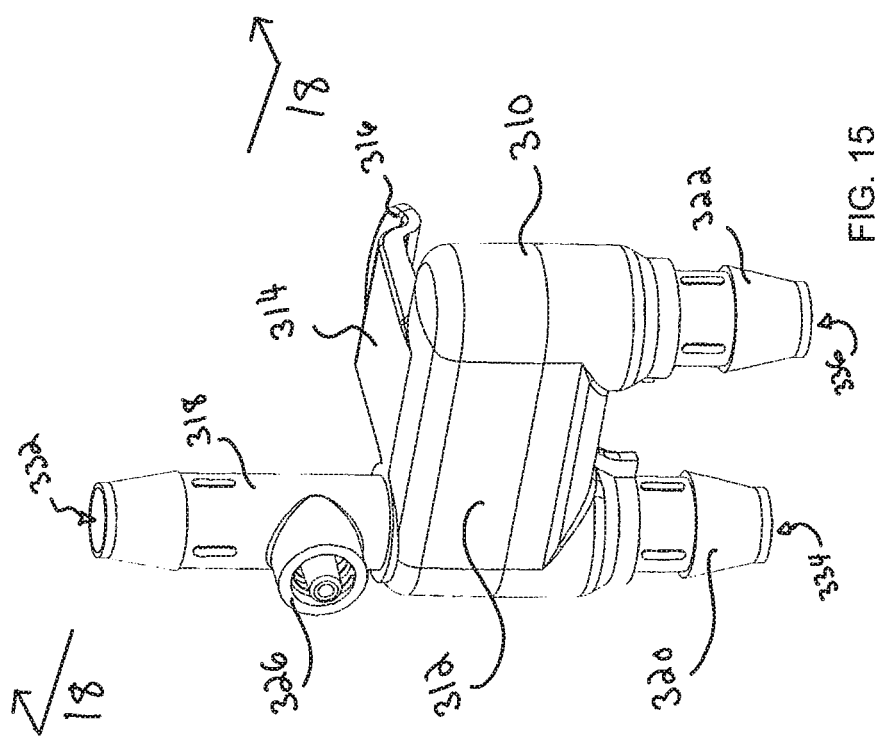
FIG. 15 depicts a perspective view of a fluid input fitting of the disposable assembly of FIG. 11.
Figure 16:
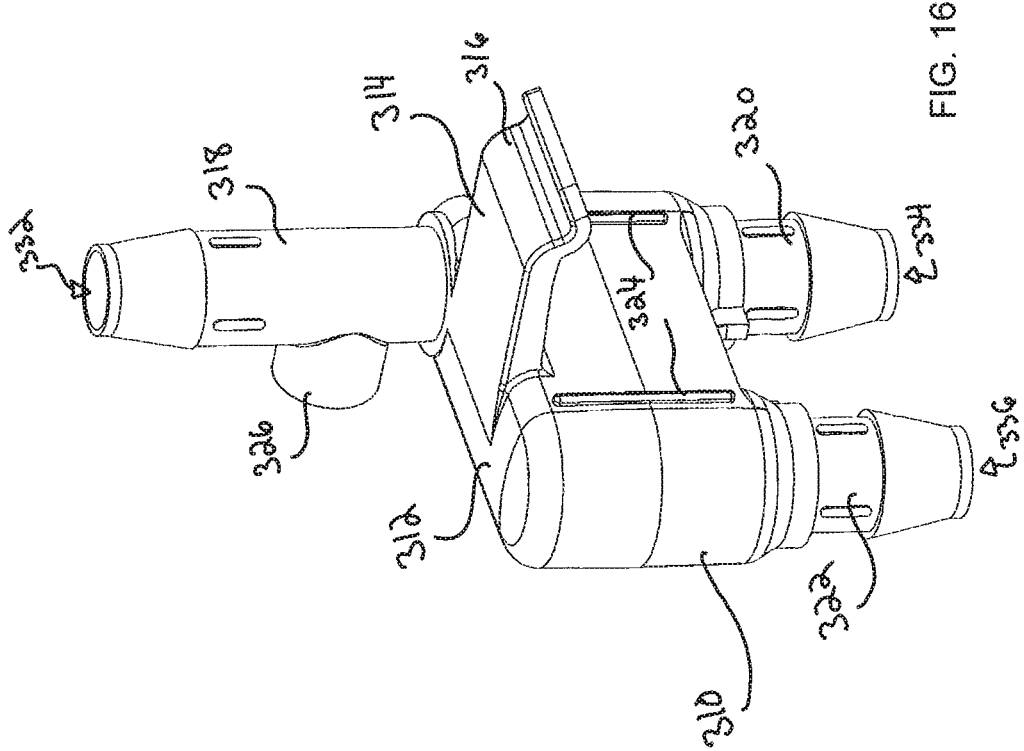
FIG. 16 depicts another perspective view of the fluid input fitting of FIG. 15.
Figure 17:
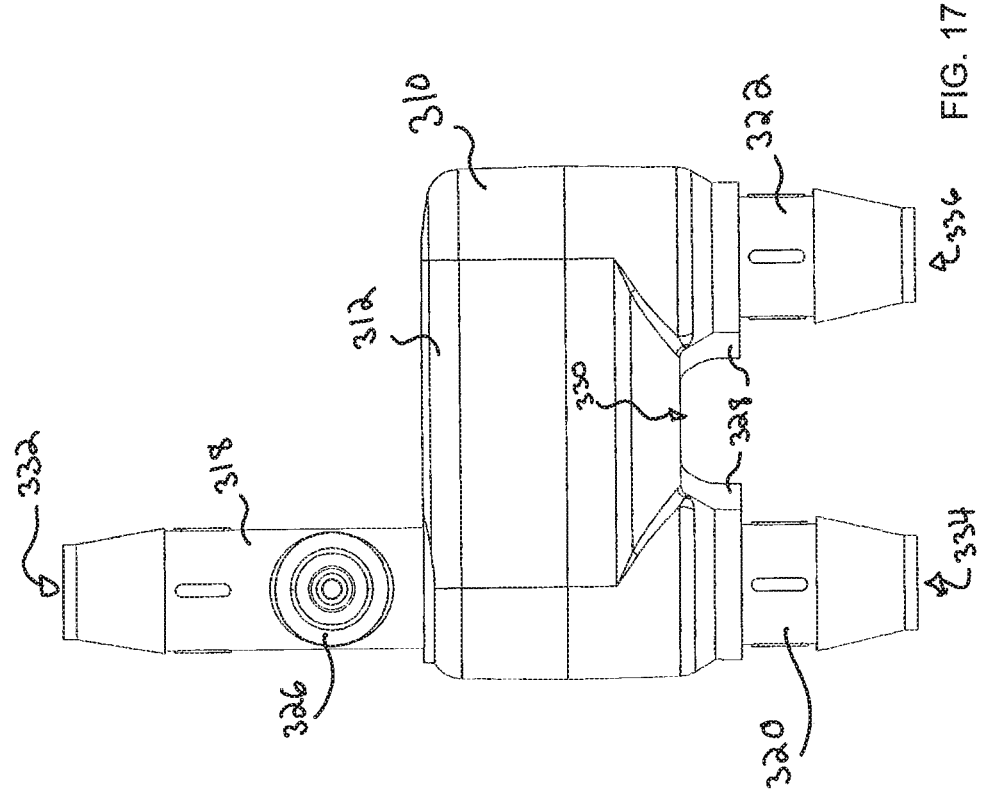
FIG. 17 depicts a front elevational view of the fluid input fitting of FIG. 15.

As best seen in FIGS. 11-12, sensing tube (304) and bypass tube (306) extend from fluid input fitting (310) toward fluid output fitting (350) in order to define an insert opening (308). As will be described in greater detail below, disposable assembly (300) may be attached to reusable assembly (200) such that arched projection (260) of reusable assembly (200) extends through insert opening (308) defined by disposable assembly (300).

FIGS. 23A-23D show an exemplary coupling of disposable assembly (300) with reusable assembly (200). In the following example, disposable assembly (300) is not yet coupled with input fluid tube (34) of output fluid tube (45). However, it should be understood that disposable assembly (300) may be already connected to catheter assembly (30) prior to coupling with reusable assembly (200).

Figure 23A:
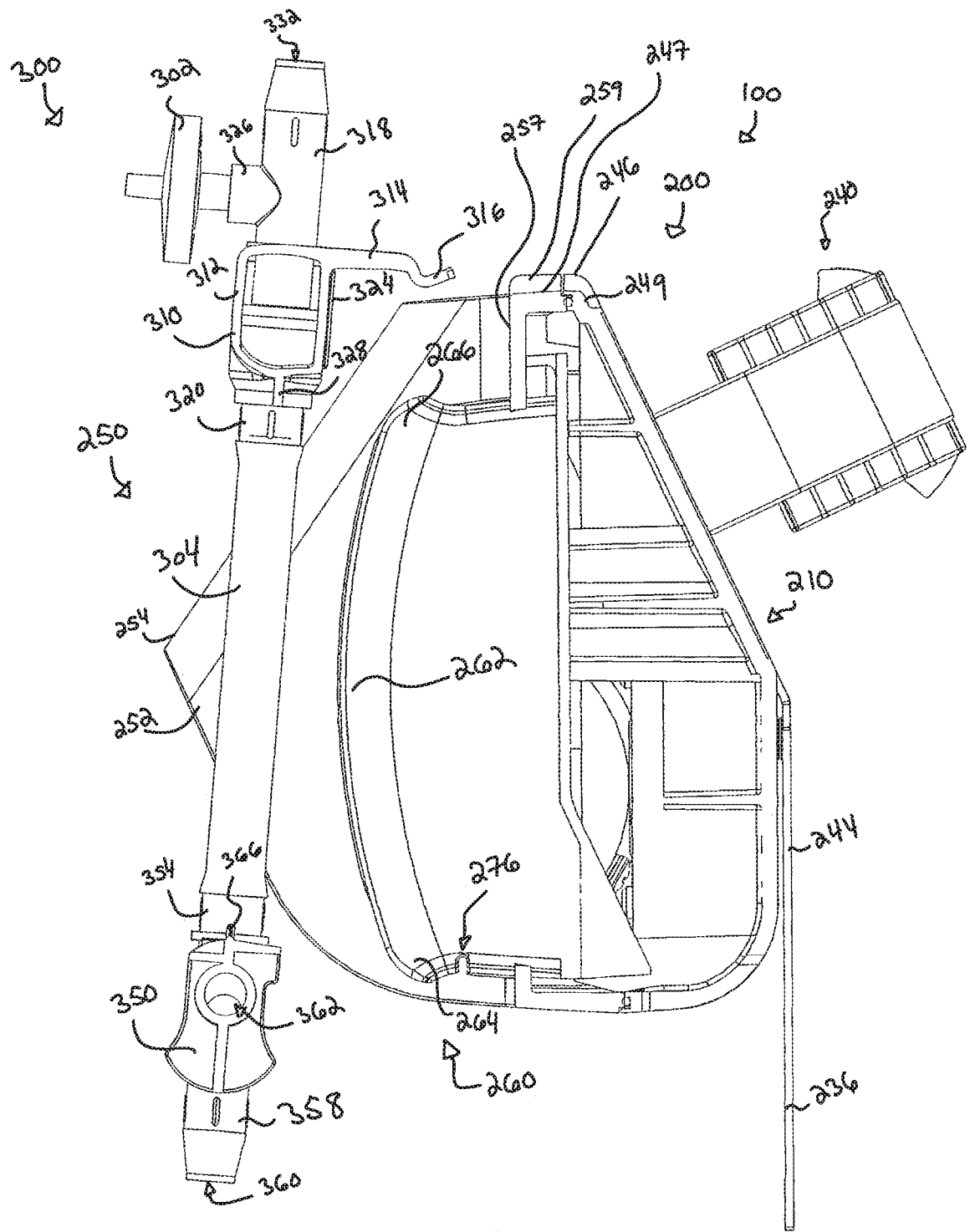
FIG. 23A depicts a cross-sectional side view of the disposable assembly of FIG. 11 aligned with the reusable assembly of FIG. 5 in preparation of coupling with each other, taken along line 23-23 of FIG. 3.

FIG. 23A shows disposable assembly (300) oriented in preparation for attachment with reusable assembly (200). Fluid input fitting (310) is positioned adjacent to upwardly presented nub (266) of arched projection (262); while fluid output fitting (350) is positioned adjacent to downwardly presented nub (264) of arched projection (262). Additionally, resilient arm (314) is facing toward guide rails (259, 246) of reusable assembly (200). In particular, resilient arm (314) is aligned between pairs of guide rails (259, 246) such that arched projection (262) is laterally aligned to receive insert opening (308) defined by sensing tube (304) and bypass tube (306).

Figure 23B:
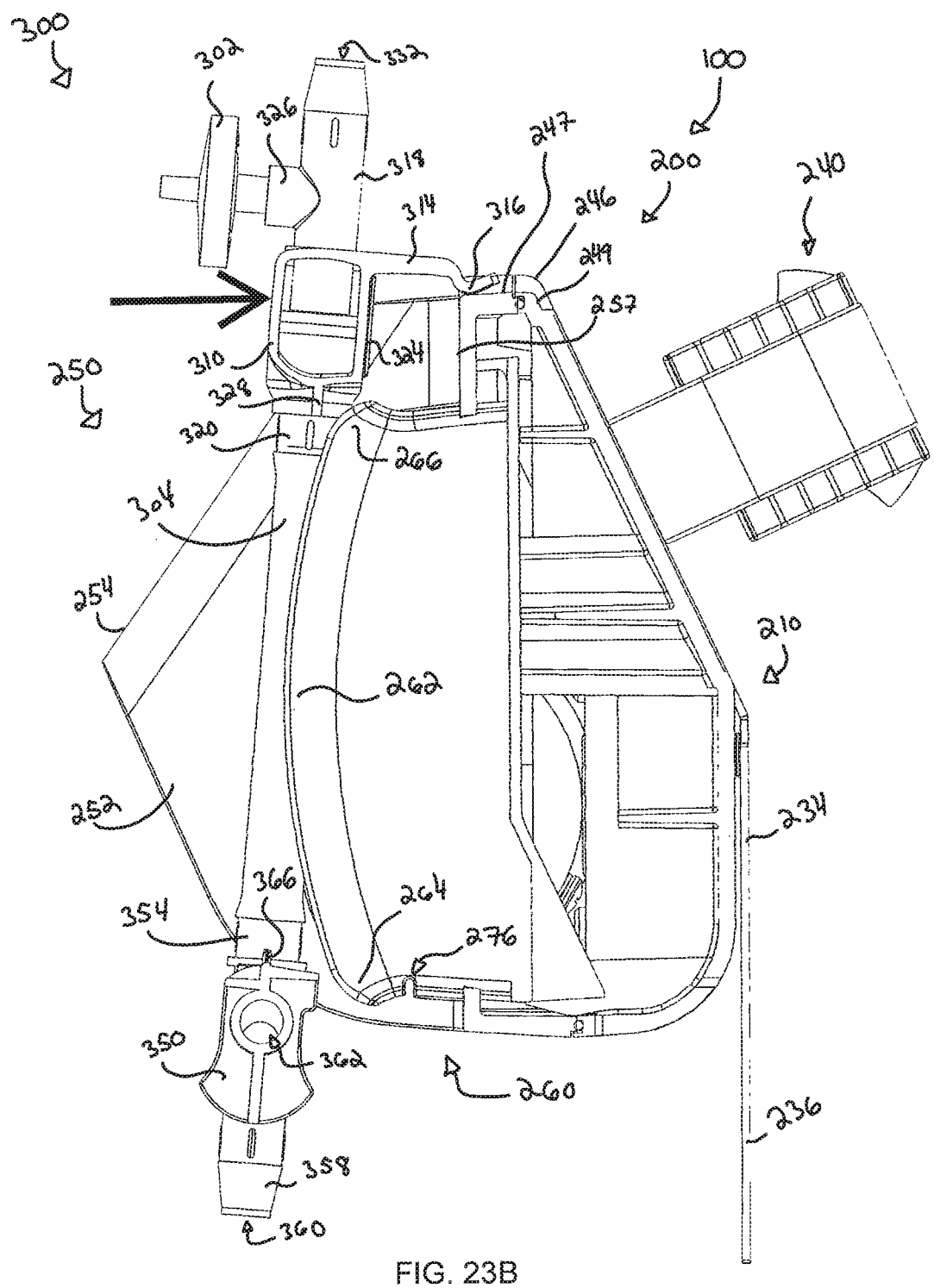
FIG. 23B depicts a cross-sectional side view of the disposable assembly of FIG. 11 aligned with and partially inserted toward the reusable assembly of FIG. 5 in preparation of coupling with each other, taken along line 23-23 of FIG. 3.
Figure 23C:
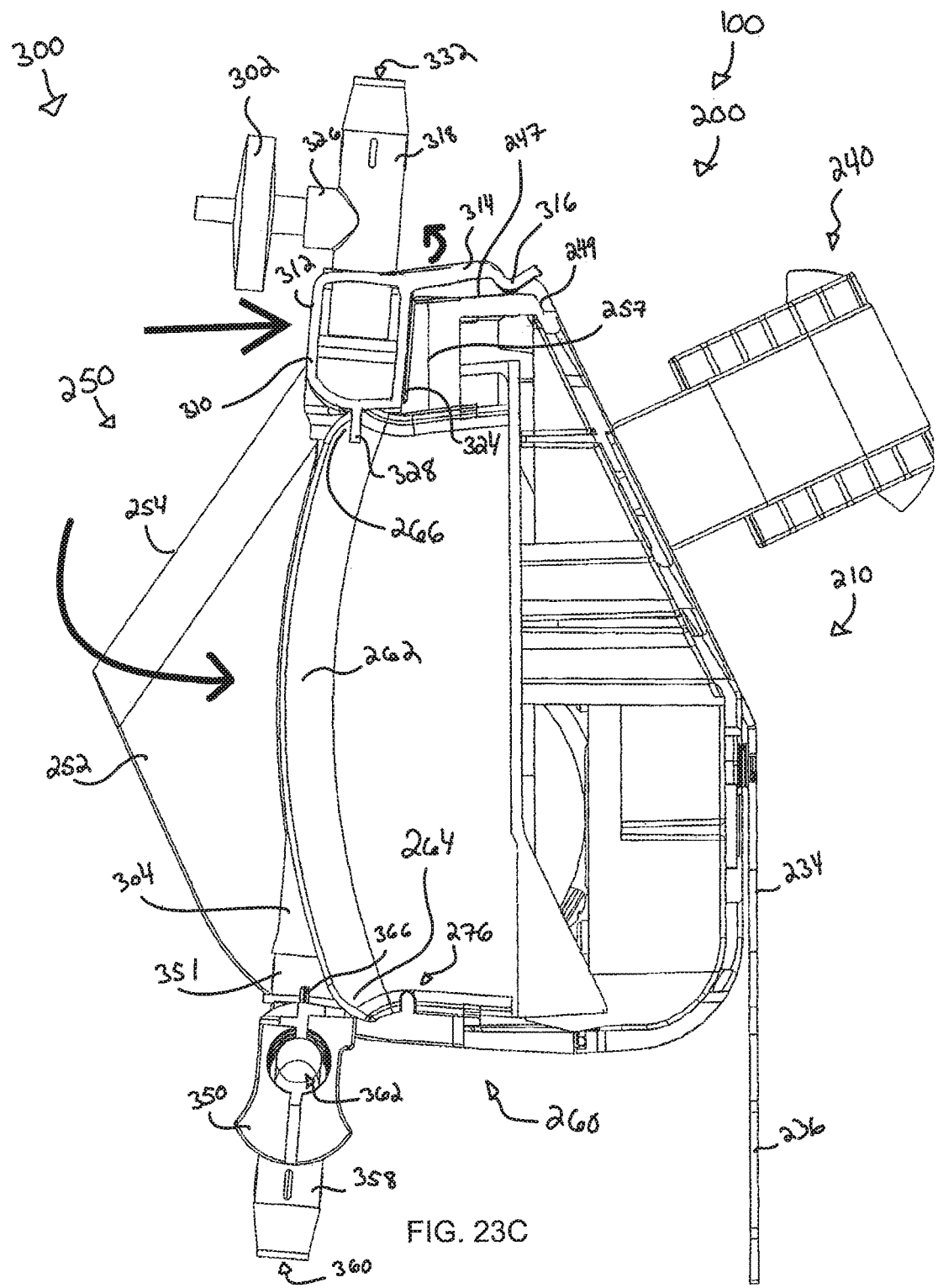
FIG. 23C depicts a cross-sectional side view of the disposable assembly of FIG. 11 aligned with and further partially inserted toward the reusable assembly of FIG. 5 in preparation of coupling with each other, taken along line 23-23 of FIG. 3.

FIG. 23B shows disposable assembly (300) inserted toward reusable assembly (200) such that downwardly presented projection (316) of resilient arm (314) is between guide rails (259) and abuts against contact wall (247). Additionally, arched projection (262) initially receives inserted opening (308) defined by sensing tube (204) and bypass tube (306). FIG. 23C shows disposable assembly (300) further inserted toward reusable assembly (200) such that arched guide members (328) make contact with upwardly presented numb (266). Additionally, disposable assembly (300) is pushed downwardly to accommodate insert opening (308) through arched projection (262), that resilient arm (314) flexes due to contact between downwardly presented projection (316) and contact wall (247).

Figure 23D:
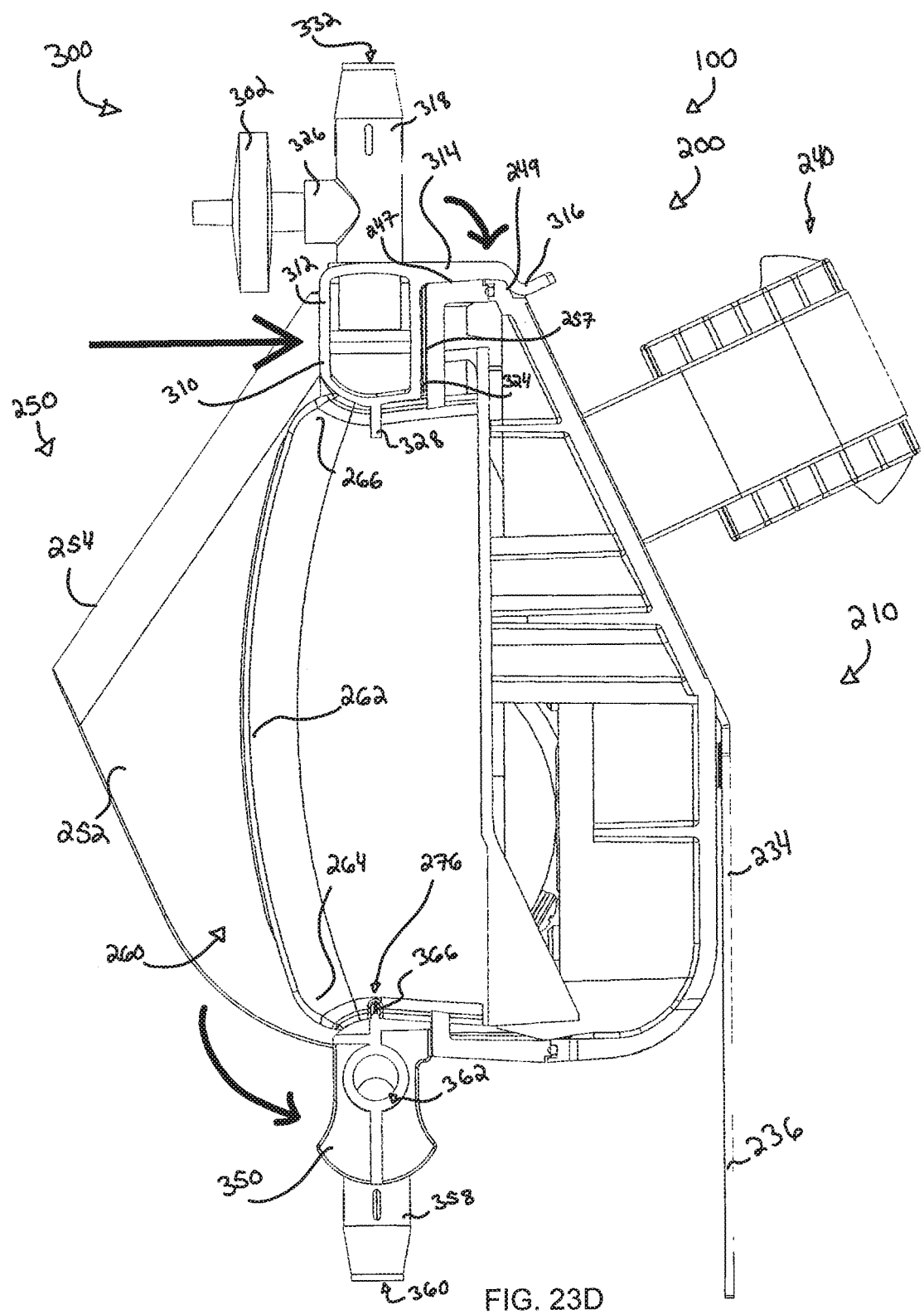
FIG. 23D depicts a cross-sectional side view of the disposable assembly of FIG. 11 coupled with the reusable assembly of FIG. 5, taken along line 23-23 of FIG. 3.

FIG. 23D shows disposable assembly (300) fully inserted toward reusable assembly (200). At this point, resilient arm (314) snaps from the flexed position to the relaxed position due to downwardly presented protrusion (316) sliding against slanted wall (249) of distal assembly (210). Resilient arm (314) may rest flush against contact wall (247). Arched guide members (328) rest on a portion of arched projection (262) distal from upwardly presented nub (266). As seen between FIGS. 23C-23D, resilient tab (366) flexes due to contact against downwardly presented nub (264), then returns to its relaxed position once positioned within cutout (276) of downwardly presented nub (264). Additionally, as the position shown in FIG. 23D, it should be understood that protrusion (364) of fluid output fitting (350) is located within notch (278) of downwardly presented nub (264). Resilient tab (366) and protrusion (364) rest within cutout (276) and notch (278) respectively in order to sufficiently locate and lock the position of disposable assembly (300) relative to reusable assembly (200). Additionally, contact ribs (324) rest flush against mating surface (257).

If an operator desires to remove disposable assembly (300) from reusable assembly (200), they may grasp fluid output fitting (350) via gripping ribs (352) and pull proximally such that resilient tab (366) snaps out of cutout (276) and such that resilient arm (314) snaps downwardly presented protrusion out of contact with slanted wall (249).

The various locating features described above may help ensure consistent and uniform attachment of disposable assembly (300) relative to reusable assembly (200). As described above, consistent and uniform attachment of disposable assembly (300) relative to reusable assembly (200) may help ensure an accurate placement of sensing tube (304) relative to pinch rod (228) and volume sensor (330). Therefore, fluid management assembly (320) may more accurately measure discrete amounts of fluid volume accumulated within sensing tube (304) by using the level at which fluid was filled within sensing tube channel (232) of fluid level sensor (230).

FIGS. 24A-24D show an exemplary fluid output monitoring process of fluid output measuring device (100). FIG. 24A shows disposable assembly (300) properly, attached to reusable assembly (200), while actuating member (224) is positioned in the open position relative to pinch rod (228). It should be understood that, at the position shown in FIG. 24A, fluid may travel from catheter (32), through input fluid tube (34), input channel (332) and flow regulating orifice (319) of flow regulating barb fitting (318), fluid chamber (330) of body (312), sensing tube (304), output channel (360) of fluid output fitting (350), output fluid tube (45), and into collection bag (40).

Once an operator is ready to start monitoring fluid output, the operator may instruct fluid output measuring device (100) to monitor fluid output via user input (258) of graphic user interface (255). Once, control assembly (280) receives operator instruction to monitor fluid, control assembly (280) may drive actuating member (224) to the closed position relative to pinch rod (228) as shown in FIG. 24B. Control assembly (280) may also start a timer at this moment. It should be understood that, at the position shown in FIG. 24B, fluid may travel from catheter (32), through input fluid tube (34), input channel (332) and flow regulating orifice (319) of flow regulating barb fitting (318), fluid chamber (330) of body (312), and accumulate within sensing tube (304). Specifically, fluid may accumulate within the portion of sensing tube (304) located above pinch rod (228).

Next, as shown in FIG. 24C fluid output measuring device (100) allows fluid to accumulate within sensing tube (304) toward the portion of sensing tube (304) located adjacent to and within the confines of sensing tube channel (232). Once fluid within sensing tube (304) reaches the confines of sensing tube channel (232), fluid level sensor (230) may send a signal to control assembly (280) indicating the maximum vertical level fluid reached within sensing tube channel (232) as detected by fluid level sensor (230).

As shown in FIG. 24D, control assembly (280) may signal to solenoid assembly (225) to drive actuating member (224) away from pinch rod (228) to the open position, so that accumulated fluid may drain from sensing tube (304), through output channel (360) of fluid output fitting (350), through output fluid tube (45), and within/into collection bag (40). Control assembly (280) may then signal to solenoid assembly (225) to drive actuating member (224) toward pinch rod (228) to the closed position, as shown in FIG. 24B in order to start the accumulation process again. It should be understood that, once solenoid assembly (225) is driven back to the closed position, control assembly (280) may restart the timing processes to determine how long it takes fluid to accumulate within sensing tube (304). Therefore, the fluid output monitoring process may start again, and cycle thorough the above described process until control assembly (280) is instructed otherwise by user input (258) of graphic user interface (255).

It should be understood that the amount of discrete accumulated fluid stored within sensing tube (304) may be substantially small relative to the size of collection bag (40). For example, sensing tube (304) may be configured to store discrete accumulated fluid amounts of 1 ml+/−0.10 ml before the fluid reaches fluid level sensor (230). Alternatively, sensing tube (304) may be configured to store any other suitable level of accumulated fluid before the fluid reaches fluid level sensor (230). By way of further example only, sensing tube (304) may be configured to store approximately 1 ml of fluid to approximately 2 ml of fluid before the fluid reaches fluid level sensor (230). It should be understood that, in the present example, it may not take a substantial amount of a time for enough fluid to accumulate in sensing tube (304) to a level sufficient to reach fluid level sensor (230). As such, solenoid assembly (225) may be driving actuating member (224) from the closed position, to the open position, and back to the closed position at high frequencies.

As described above, the maximum vertical level fluid reaches within sensing tube channel (232) may be indicative of a specific fluid volume accumulated within sensing tube (304). Control assembly (280) may store the value indicative of the discrete volume accumulated within sensing tube (304) as well as the time it took to fill sensing tube (304) to that particular discrete volume. Control assembly (80) may index these volumes and times relative to each other, such that data points representing the third fluid accumulation cycle is stored adjacent to data points representing both the second fluid accumulation cycle and the fourth fluid accumulation cycle. Control assembly (280) may use these data points in any suitable number of calculations in order to determine volume within collection bag (40), volumetric flow rate through catheter assembly (30), and change in volumetric flow rate within catheter assembly (30). These values may also be used in order to calculate other specific risk factors that will be apparent to one having ordinary skill in the art in view of the teachings herein. Some exemplary calculations will be described in greater detail below.

Figure 25:
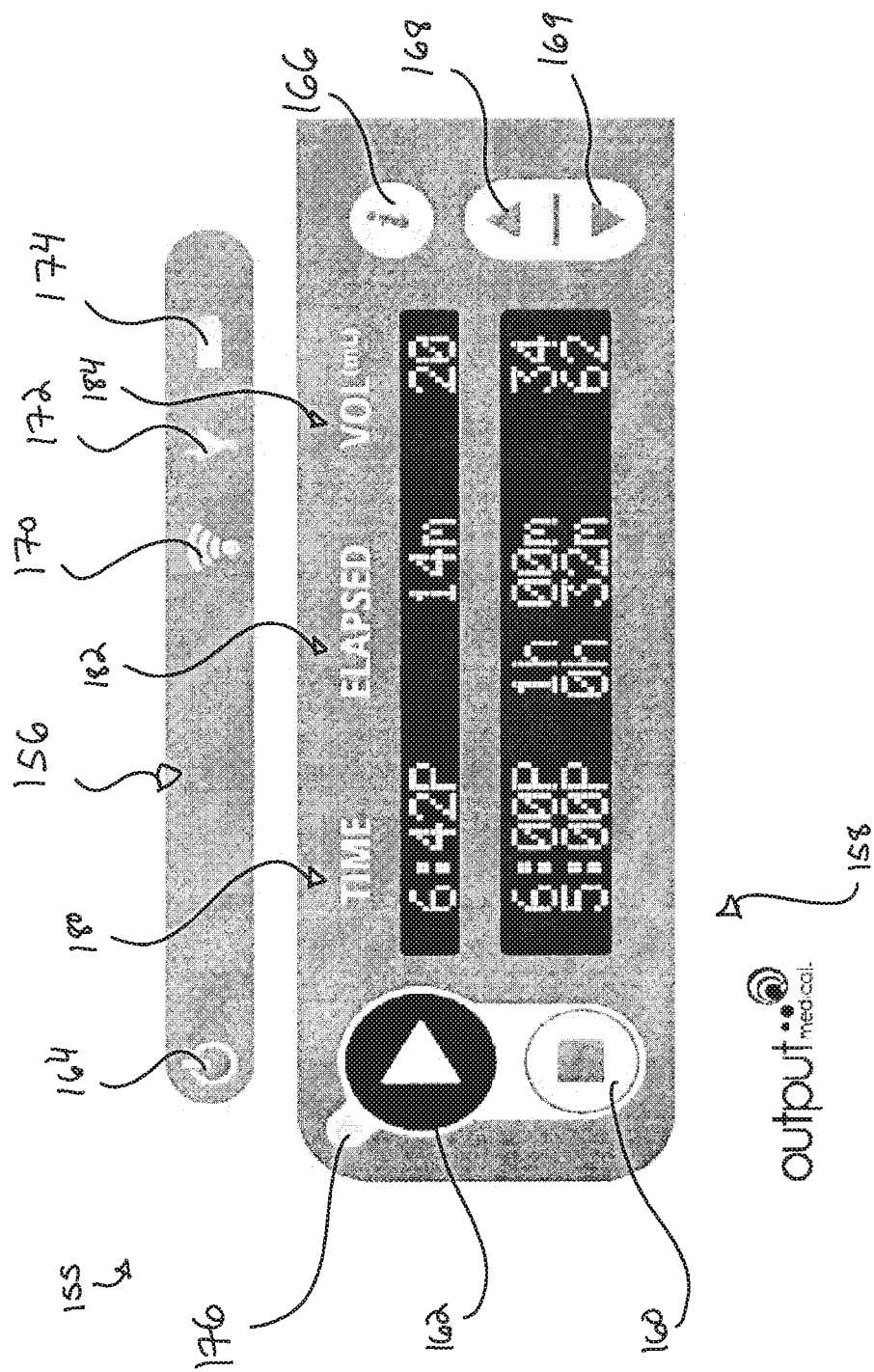
FIG. 25 depicts a front elevational view of an exemplary user interface that may be readily incorporated into the fluid output measuring device of FIG. 2.

FIG. 25 shows an alternative graphic user interface (155) that may be readily incorporated into fluid output measuring device (100) in replacement of graphic user interface (255) described above. Therefore, graphic user interface (155) may send operator instructions to control assembly (280), as well as receive and display data from control assembly (280). Similar to graphic user interface (255), graphic user interface (155) includes a display (156) and a user input (158), which may be substantially similar to display (256) and user input (258) described above, respectively, with differences elaborated below.

User input (158) includes a start button (162), a stop button (160), a power button (164), an info button (166), a scroll up button (168), and a scroll down button (169).

Display (156) includes a wireless indicator (170), a wall power indicator (172), a battery indicator (174), a monitoring LED (176), a time stamp display column (180), a time elapsed display column (182), and a volume column (184).

Power button (164) may be pressed in order to power fluid output measuring device (100) on and off. While on, start button (162) may be pressed in order to start the fluid output monitoring process described above, while stop button (160) may be processed in order to stop the fluid output monitoring process described above. Info button (166) may be pressed to selectively change the information shown in display (156), such as if errors occur, but an operator still wishes to see previously collected data points. Info button (166) may also be used for any other suitable purpose that would be apparent to one having ordinary skill in the art in view of the teachings herein. The scroll up and down (168, 169) buttons may be pressed in order to scroll through collected data points shown on display (156) or for any other suitable purpose that would be apparent to one having ordinary skill in the art in view of the teachings herein.

Wireless indicator (170) may indicate to an operator if/when fluid output measuring device (100) is in wireless communication with another device, such as server (50) described above. Wall power indicator (172) may indicate to an operator if fluid output measuring device (100) is connected to an external source of power, while battery indicator (174) may indicate if fluid output measuring device (100) is using battery (216) or how much battery life is left in battery (216).

Time stamp column (180), time elapsed column (182), and volume column (184) together display relevant information relating to fluid output measured during specific periods of time. For example, the top row of time stamp column (180) may indicate the current time, while lower rows of the time stamp column (180) may indicate previous times during the fluid output monitoring period. The elapsed time (182) may indicate the time difference between the matching row of the time stamp column (180) and the row directly under the matching time stamp column (180). The volume column (184) may indicate the amount of fluid output measured during the matching elapsed time (182) row. Therefore, an operator may know the time related to a specific data point, the time elapsed from the previous data point, as well as the total volume collected during the time between the specific data point and the previous data point. An operator may further use the scroll up bottom (168) and the scroll down button (169) in order to view various rows of data points along columns (180, 182, 184).

III. Exemplary Operation of Fluid Output Measuring Device

Figure 26:
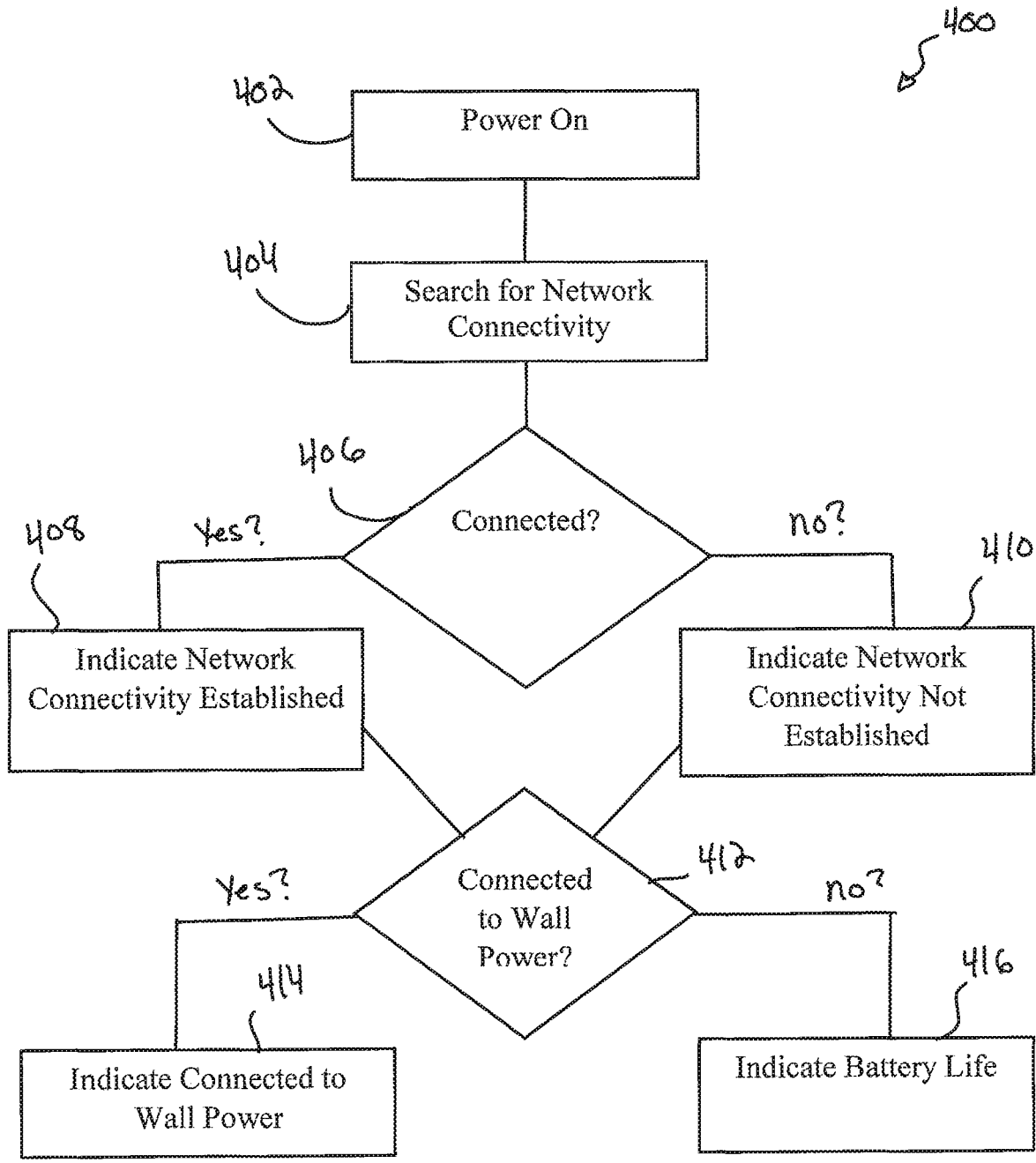
FIG. 26 depicts a schematic flow diagram of exemplary use of the fluid output measuring device of FIG. 2.
Figure 27:
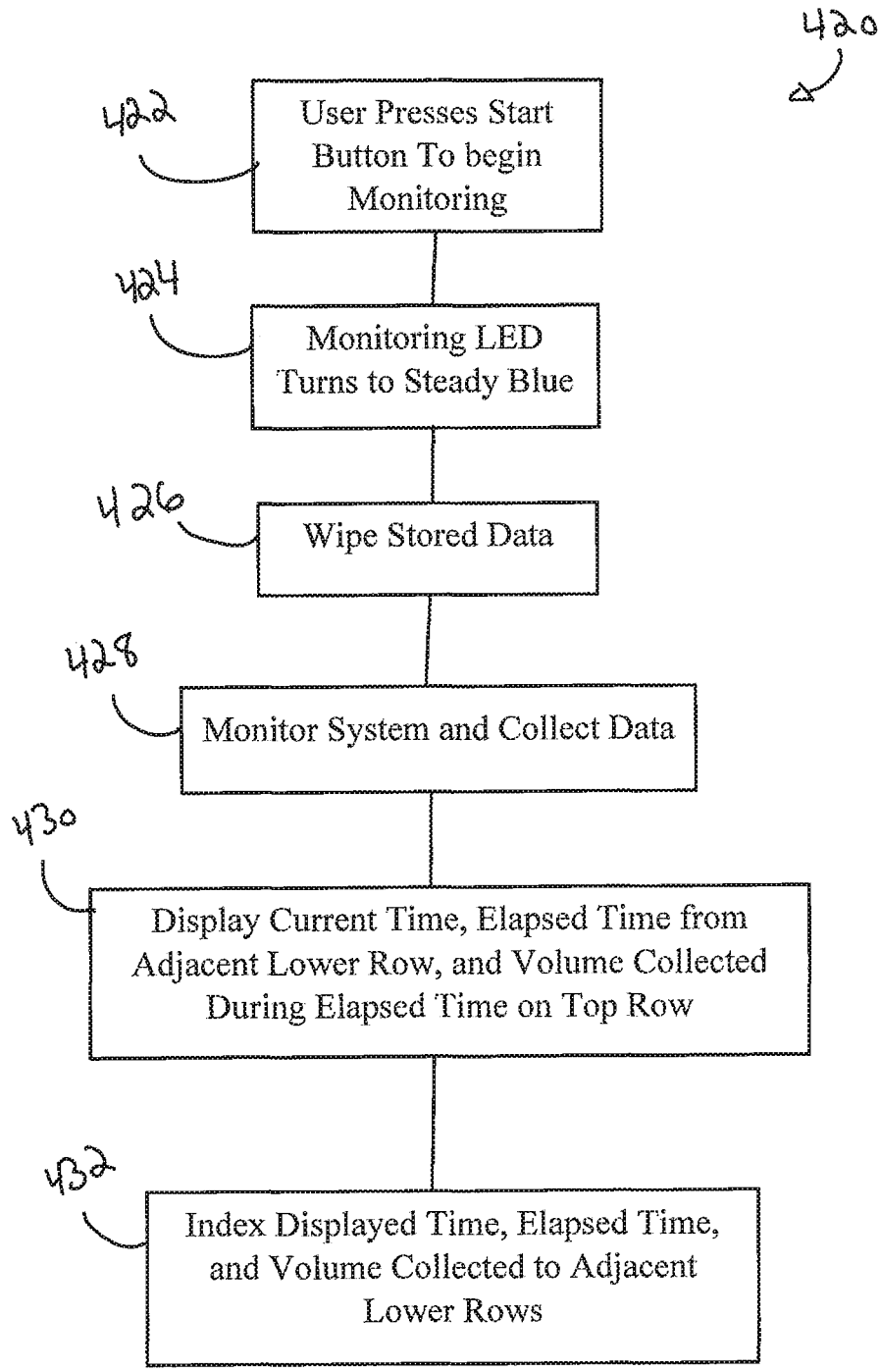
FIG. 27 depicts a schematic flow diagram of further exemplary use of the fluid output measuring device of FIG. 2.
Figure 28:
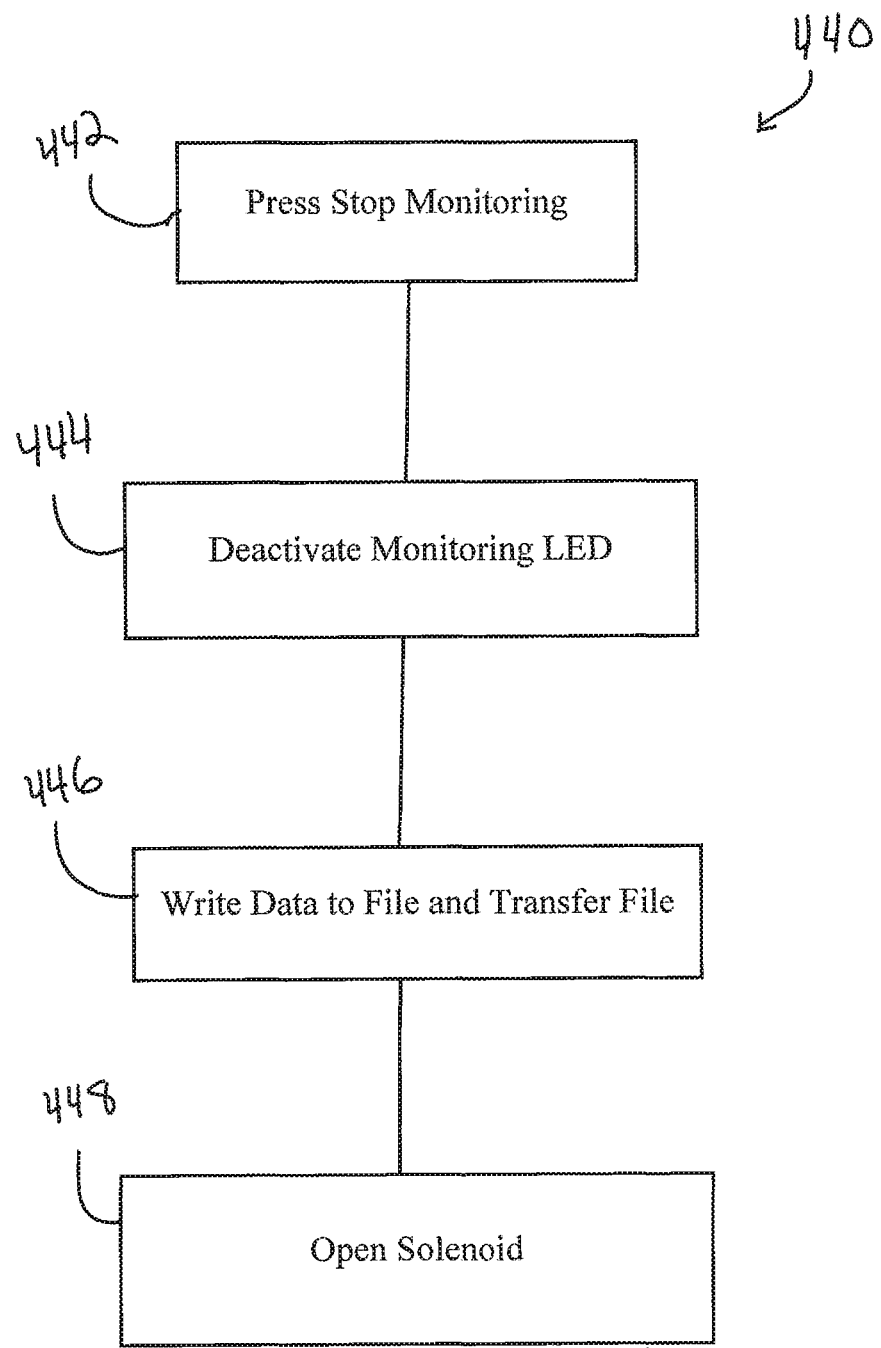
FIG. 28 depicts a schematic flow diagram of yet further exemplary use of the fluid output measuring device of FIG. 2.

FIGS. 26-28 show a flow chart representing the exemplary use of fluid output measuring device (100) in conjunction with graphic user interface (155) described above. FIG. 26 shows a flow chart representing an exemplary power on process (400), FIG. 27 shows a flow chart representing an exemplary data collection process (420), and FIG. 28 shows a flow chart representing an exemplary cease monitoring process (440). While the current flow chart process (400, 420, 440) are shown and described as separate acts, it should be understood they may be used in combination with each other in one cumulative process.

First, as shown in FIG. 26, an operator may press the power button (164) in order to power on (402) fluid output measuring device (100). While booting up, control assembly (280) may search for wireless network connectively (404) in order to establish a connection with server (50) or any other suitable device. Next, fluid output measuring device (100) may determine whether a wireless connection was made with server (50). If a connection is made, wireless network indicator (170) may indicate that network connectively has been established (408). However, if after a predetermined time or predetermined amount of connection attempts, fluid output measuring device (100) cannot connect to a wireless network, wireless network indicator (170) may indicate network connectively cannot be established (410).

Next, fluid output measuring device (100) may determine whether it is connected to an external source of power (412). If fluid output measuring device (100) is connected to an external source of power, it may indicate this connection (414) by activating wall power indicator (172). If fluid output measuring device (100) is not connected to an external source of power, it may indicate that battery life is being used (416) by activated battery indicator (174).

With fluid output measuring device (100) powered on, an operator may wish to start the data collection process (420). First, an operator may press start button (162) to being fluid output monitoring (422) as described above. Next, monitoring LED (176) may turn to steady blue (424) in order to indicate and confirm to an operator that fluid output monitoring is activated. Next, fluid output measuring device (100) may wipe previously stored data from memory (426). Once memory is wiped, fluid output measuring device (100) may monitor fluid output and collect data as described above. As shown in block (430), with fluid output measuring device (100) monitoring fluid output and collecting data, display (156) may display the current time on the top row of time stamp column (180), display the time elapsed between the time on the top of time stamp column (180) and the adjacent lower row of time stamp column (180) on the top row of the time elapsed column (182), and also show the volume collected by fluid output measuring device (100) during the time elapsed.

As shown in block (432), after a predetermined period of time such as on the hour mark, graphic user interface (155) may index the displayed time, elapsed time, and volume collected to adjacent lower rows. Fluid output measuring device (100) may repeat the steps shown in blocks (430, 432), until an operator wishes to cease the monitoring process (440) shown in FIG. 28.

When an operator decides to cease the monitoring process (440), first the operator may press the stop button (160) as shown in block (442). In response, monitoring LED (176) will deactivate as shown in block (444). Next, control assembly (280) may write accumulated data to a file and transfer the file to server (50) and or mobile storage device, as shown in block (446). With the file transferred, fluid output measuring device (100) may actuate solenoid to the open position, as shown in block (448).

IV. Exemplary Method of Data Analysis of Fluid Output Measuring Device

Figure 31:
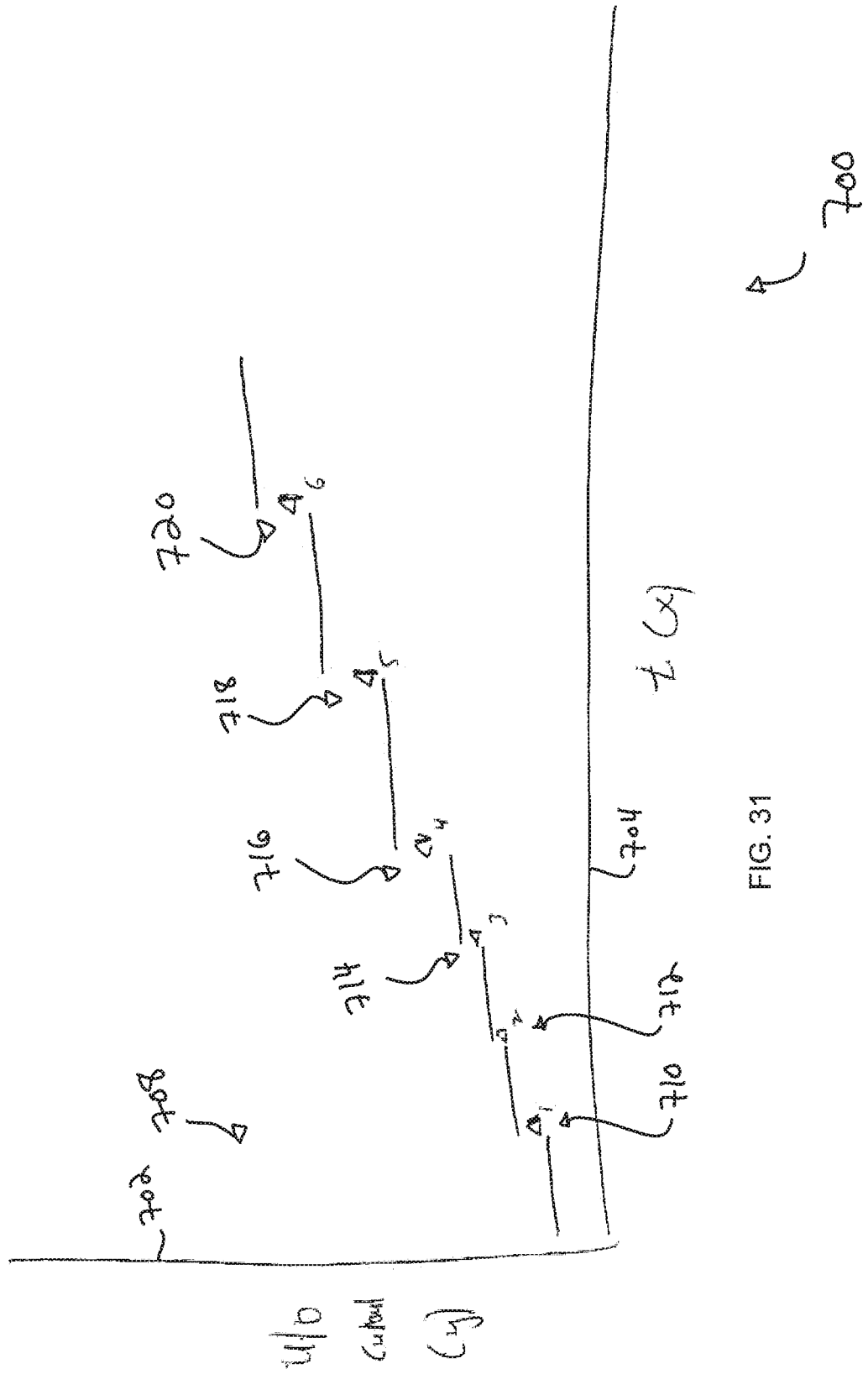
FIG. 31 depicts a graph representing a cumulative fluid output from the fluid output measuring device of FIG. 2 over a period of time.

FIGS. 29-31 show an exemplary accumulation of data obtained by fluid output measuring device (100). FIG. 29 shows a plot (500) of individual discrete fluid output accumulations (510) measured with a y-axis (502) in milliliters (mL). The x-axis (504) is measured in time. The length of each individual discrete fluid output accumulation (510) relates to how long it took sensing tube (304) to fill up to the volume in milliliters (mL). Y-axis (502) is also marked with an upper release range (506), and a lower release range (508). Upper and lower release ranges (506, 508) may correspond to the upper and lower measuring values defined by vertical measuring limits of sensing tube channel (232) of fluid level sensor (230). Therefore, each discrete fluid output accumulation (510) may, have a value within upper and lower release ranges (506, 508). The length of each individual discrete fluid output accumulation (510) may also be obtained from the time measured by control assembly (280) to fill each individual discrete fluid output accumulation (510).

FIG. 30 shows the same exemplary accumulation of data obtained by fluid output measuring device (100), except in a plot (600) from the perspective of collection bag (40). Therefore, individual discrete fluid output accumulations (610) may be representative of individual discrete fluid output accumulation (510) entering collection bag (40), where the x-axis (604) is time and the y-axis (602) is volume in milliliters (mL) of fluid within collection bag (40). Because collection bag (40) receives individual discrete fluid output accumulations (610) only after fluid is filled within sensing tube (304) to a predetermined range, collection bag (40) increases its volume very similar to a step-function. A step-function is a piecewise function containing all "pieces that do not change across the y-axis. The contact pieces are observed across the adjacent intervals of the function.

FIG. 30 shows a plot (700) of the first seven data points from plot (600), where the $\Delta_1$, $\Delta_2$, $\Delta_3$, $\Delta_4$, $\Delta_5$, and $\Delta_6$ are labeled as (710, 712, 714, 716, 718, 720) respectively and represent an estimated volumetric flow rates for times to fill up sensor tube (304) within the release range (506, 508) for each discrete fluid accumulation. Y-axis (702) is substantially the same as y-axis (602); while the x-axis (704) is substantially the same the x-axis (604) described above. Therefore, an estimated volumetric flow rate may be written as the following, in mL per second:

$$\Delta_1 = m_1 = \frac{y_2 - y_1}{x_2 - x_1}; \text{ or}$$

$$m_{ab} = \frac{y_b - y_a}{x_b - x_a}$$

Fluid output flow, however, is not just a function of fluid production, but also tubular fluid dynamics as the fluid passes through the catheter and into disposable unit (300). As mentioned above, flow regulating orifice (319) may limit the fluid output into sensing tube to a maximum velocity with laminar flow; while the minimum velocity may be 0. Because of flow regulating orifice (319) limiting the maximum flow of fluid into disposable assembly (300), parameters may be established in which the maximum and minimum flow rate may be set. Therefore, the parameters may set flow rates ranging from 0 mL/s to $\Delta_{max}$ mL/s. In other words, all the estimated volumetric flow rates labeled as (710, 712, 714, 716, 718, 720) must be between 0 mL/s and $\Delta_{max}$ mL/s.

Based off data shown in FIGS. 30 and 31, and based on parameters established by maximum and minimum flow rates, the step functions can then approximate slope over set time intervals depending on the level of integration. LaPlace and Fourier transformations can approximate a slope function over time through aggregating step functions over time. Control module (280) may manipulate data with LaPlace and Fourier transformations to approximate a slope function over time through aggregating step functions over time. The integral equation can then provide trend analysis to define slopes and inflection points of change, elucidating first, second, and third order equations. These data points can then integrate into predictive and diagnostic models that incorporate existing clinical data to ascertain statistically significant, independent clinical risk factors. For example, control module (280) can identify points of rate changes above set parameters over the course of twenty-four hours and correlate that data with serum creatinine changes over the course of the same twenty-four hours. These correlations matrices can determine clinically significant action points in real time upon retrospective review. The transformation functions can approximate slope functions over a range of time intervals ranging from one hour, or sixty minutes, to longer or shorter intervals, as well, on the order of days to minutes, respectively.

Through a retrospective analysis of the data generated through first, second, and third order equations, control module (280) can cross reference trending data points of key clinical vitals, lab values, and biomarkers, to identify statistically significant associations. Through these associations, the model can develop algorithms that quantify patient heath risk and create dynamic variance models of adjusting specificity, sensitivity as a function of clinical action taken or as a function of time or information accrued from critical vitals, lab values, and, or biomarkers.

For example, if a patient at risk of acute kidney injury develops increase volatility in their urine output and upward trending white blood cell count, the model can signal the need for additional fluid bolus. Through this model it can be identified what would be the predictive and diagnostic likelihood of acute kidney injury based upon the urine output volatility, the additional fluid, and the reading of a lab value, such as white blood cell count. These likelihood functions would vary over time and would depend on statistically significant associations developed through retrospective chart review of prospective clinical studies studying such correlations.

The average rate of urine output may be established as follows:

$\int_0^t m_{ab}$=average rate of urine output or rate over time interval "$t$"

$t=b-a$.

$\Sigma \int_{t1} m_1 \int_{t2} m_2 \int_{t3} m_3 \int_{t4} m_4$=Total Volume

A risk score may be established as follows:

$\int_0^t m_{ab} \int_0^t wbc \int_0^t sCr = AKI$ risk Score where wbc represents white blood cell count change over time; and sCr represents serum creatinine change over time.

In this context, risk factors $RF_1$ and $RF_2$ may be established as follows:

$wbc = RF_1$ $sCr = RF_2$ $\int RF_x > 1$

Where I represents interval change of risk factor over time;

If the change in the risk factor, $\int RF_x$, is greater than the assumed change in the clinical variable, I, over the interval, that risk factor becomes a significant data point and should be incorporated as a significant change in the AKI decision model.

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways and incorporate a myriad of clinically significant risk factors. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus configured to measure fluid comprising: (a) a disposable assembly comprising: (i) a fluid input port configured to receive fluid from a fluid source, (ii) a fluid output port configured to deliver fluid received from the fluid input port to a fluid collection area, and (iii) a tube configured to provide fluid communication between the fluid input port and the fluid output port; (b) a reusable assembly comprising: (i) a housing, (ii) a fluid management assembly that is configured to transition between an open position and a closed position, wherein the fluid management assembly is configured to prevent fluid from traveling past the tube to the fluid output port in the closed position, and (iii) a sensing assembly configured to sense fluid accumulating within the tube while the fluid management assembly is in the closed position, wherein the sensing assembly is configured to drive the fluid management assembly from the closed position to the open position when the sensing assembly detects fluid within the tube at a predetermined range.

Example 2

The apparatus of Example 1, wherein the predetermined range is a predetermined height range.

Example 3

The apparatus of Example 1, wherein the predetermined range is a predetermined volume range.

Example 4

The apparatus of any one or more of Examples 1-3, wherein the housing comprises a graphic user interface facing an upward angle.

Example 5

The apparatus of any one or more of Examples 1-4, wherein the housing comprises a collection bag bracket configured to couple with the fluid collection area.

Example 6

The apparatus of any one or more of Examples 1-5, wherein the disposable assembly further comprises a plurality of gripping ribs.

Example 7

The apparatus of any one or more of Examples 1-6, wherein the disposable assembly further comprises a distally extending arm.

Example 8

The apparatus of any one or more of Examples 1-7, wherein the fluid input port further comprises a bacterial air vent.

Example 9

The apparatus of any one or more of Examples 1-8, wherein the fluid input port defines a flow regulating input channel in fluid communication with the fluid source.

Example 10

The apparatus of Example 9, wherein the fluid regulating input channel terminates into a flow regulating orifice.

Example 11

The apparatus of Example 10, wherein the flow regulating orifice has a smaller cross-sectional geometry than the flow regulating input channel.

Example 12

The apparatus of any one or more of Examples 1-11, wherein the sensing assembly comprises an ultrasonic sensor.

Example 13

The apparatus of any one or more of Examples 1-12, wherein the reusable assembly comprises a disposable mounting assembly, wherein the disposable assembly is configured to consistently attach with the reusable assembly via the disposable mounting assembly.

Example 14

The apparatus of any one or more of Examples 1-13, wherein the disposable mounting assembly comprises an arched protrusion.

Example 15

The apparatus of Example 14, wherein the arched protrusion terminates into an upwardly extending nub and a downwardly extending nub.

Example 16

The apparatus of any one or more of Examples 1-15, wherein the reusable assembly further comprises a control assembly, wherein the control assembly is configured to calculate the volumetric flow through the disposable assembly.

Example 17

The apparatus of Example 16, wherein the control assembly is configured to calculate the change in volumetric flow through the disposable assembly.

Example 18

The apparatus of either Examples 16 or 17, wherein the control assembly is configured to calculate the volume of fluid within fluid collection area based off the volumetric flow through the disposable assembly.

Example 19

The apparatus of any one or more of Examples 16-18, wherein the control assembly is configured to calculate risk factors based on the volumetric flow through the disposable assembly.

IV. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus configured to measure fluid comprising:
   (a) a disposable assembly comprising:
      (i) a fluid input fitting configured to receive fluid from a fluid source, the fluid input fitting including a first input port, a first output port, and a second output port,
      (ii) a fluid output fitting configured to deliver fluid received from the fluid input fitting to a fluid collection area, the fluid output fitting including a second input port, a third input port, and a third output port,
      (iii) a first tube configured to provide fluid communication between the first output port of the fluid input fitting and the second input port of the fluid output fitting, wherein the tube extends between the first output port of the fluid input fitting and the second input port of the fluid output fitting such that the tube is interposed between the first output port of the fluid input fitting and the second input port of the fluid output fitting, and
      (iv) a second tube configured to provide fluid communication between the second output port of the fluid input fitting and the third input port of the fluid output fitting; and
   (b) a reusable assembly comprising:
      (i) a housing,
      (ii) a fluid management assembly that is configured to transition between an open position and a closed position, wherein the fluid management assembly is configured to permit fluid to accumulate within the first tube by preventing fluid from traveling past the first tube to the second input port of the fluid output fitting in the closed position,
      (iii) a sensor configured to sense fluid accumulating within the first tube while the fluid management assembly is in the closed position, and
      (iv) a control assembly, wherein the control assembly is configured to send a signal to the fluid management assembly to thereby drive the fluid management assembly from the closed position to the open position when the sensor detects fluid within the first tube at a predetermined range.

2. The apparatus of claim 1, wherein the predetermined range is a predetermined height range.

3. The apparatus of claim 1, wherein the predetermined range is a predetermined volume range.

4. The apparatus of claim 1, wherein the housing comprises a graphic user interface facing an upward angle.

5. The apparatus of claim 1, wherein the housing comprises a collection bag bracket configured to couple with the fluid collection area.

6. The apparatus of claim 1, wherein the disposable assembly further comprises a distally extending arm.

7. The apparatus of claim 1, wherein the fluid input fitting further comprises a bacterial air vent.

8. The apparatus of claim 1, wherein the first input port of the fluid input fitting defines a flow regulating input channel in fluid communication with the fluid source.

9. The apparatus of claim 8, wherein the fluid regulating input channel terminates into a flow regulating orifice, wherein the flow regulating orifice has a smaller cross-sectional geometry than the flow regulating input channel.

10. The apparatus of claim 1, wherein the sensor comprises an ultrasonic sensor.

11. The apparatus of claim 1, wherein the reusable assembly comprises a disposable mounting assembly, wherein the disposable assembly is configured to consistently attach with the reusable assembly via the disposable mounting assembly.

12. The apparatus of claim 11, wherein the disposable mounting assembly comprises an arched protrusion.

13. The apparatus of claim 1, wherein the control assembly is configured to calculate a volumetric flow of fluid through the disposable assembly.

14. The apparatus of claim 13, wherein the control assembly is configured to calculate a change in the volumetric flow of fluid through the disposable assembly.

15. The apparatus of claim 13, wherein the control assembly is configured to calculate a volume of fluid within the fluid collection area based off the volumetric flow through the disposable assembly.

16. The apparatus of claim 13, wherein the control assembly is configured to calculate risk factors based on the volumetric flow through the disposable assembly.

17. The apparatus of claim 1, wherein the fluid management assembly comprises a pinch valve that is operable to pinch the first tube to thereby permit fluid to accumulate within the first tube by preventing fluid from traveling past the first tube at the pinch valve.

18. The apparatus of claim 17, wherein the first tube includes a first end, a second end, and an intermediate region extending between the first end and the second end, wherein the first end is coupled to the first output port of the fluid input fitting, wherein the second end is coupled to the second input port of the fluid output fitting, wherein the pinch valve is positioned along the intermediate region.

19. An apparatus configured to measure fluid comprising:
(a) a first assembly comprising:
  (i) a fluid input fitting configured to receive fluid from a fluid source,
  (ii) a fluid output fitting configured to deliver fluid received from the fluid input fitting to a fluid collection area,
  (iii) a first flexible tube configured to provide fluid communication between the fluid input fitting and the fluid output fitting, wherein the first flexible tube extends between the fluid input fitting and the fluid output fitting such that the first flexible tube is interposed between the fluid input fitting and the fluid output fitting, and
  (iv) a second tube configured to provide fluid communication between the fluid input fitting and the fluid output fitting; and
(b) a second assembly comprising:
  (i) a housing,
  (ii) a fluid management assembly coupled with the first flexible tube between the fluid input fitting and the fluid output fitting, wherein the fluid management assembly is configured to transition between an open position and a closed position, wherein the fluid management assembly is configured to provide accumulation of fluid within the first tube by preventing fluid from traveling through the first flexible tube to the fluid output fitting in the closed position, wherein the second tube is configured to permit fluid to travel from the fluid input fitting to the fluid output fitting while the fluid management assembly prevents fluid from traveling through the first flexible tube to the fluid output fitting,
  (iii) a sensor configured to sense fluid accumulating within the first flexible tube while the fluid management assembly is in the closed position, and
  (iv) a control assembly, wherein the control assembly is configured to send a signal to the fluid management assembly to thereby drive the fluid management assembly from the closed position to the open position in response to a signal from the sensor indicating detection of fluid within the first flexible tube by the sensor.

20. An apparatus configured to measure fluid comprising:
(a) a fluid input fitting configured to receive fluid from a fluid source;
(b) a fluid output fitting configured to deliver fluid received from the fluid input fitting to a fluid collection area;
(c) a first flexible tube configured to provide fluid communication between the fluid input fitting and the fluid output fitting, wherein the first flexible tube extends between the fluid input fitting and the fluid output fitting such that the first flexible tube is interposed between the fluid input fitting and the fluid output fitting;
(d) a valve that is configured to transition between an open position and a closed position, wherein the valve is configured to block a flow of fluid through the first flexible tube, and thereby provide accumulation of fluid within the first flexible tube, in the closed position;
(e) a sensor configured to sense fluid accumulating within the first flexible tube while the fluid management assembly is in the closed position;
(f) a control assembly, wherein the control assembly is configured to send a signal to the fluid management assembly to thereby drive the valve from the closed position to the open position in response to a signal from the sensor indicating detection of a certain amount of fluid accumulating within the first flexible tube; and
(g) a second tube configured to provide fluid communication between the fluid input fitting and the fluid output fitting separately from the first flexible tube, the second tube being configured to provide an overflow path from the fluid input fitting to the fluid output port when the valve is in the closed position.

* * * * *